(12) United States Patent  
Schulter et al.

(10) Patent No.: US 7,179,088 B2
(45) Date of Patent: Feb. 20, 2007

(54) LOBED DENTAL IMPLANT

(75) Inventors: Carl W Schulter, Memphis, TN (US); Andrew J. Schulter, Germantown, TN (US); Gary Qi, Memphis, TN (US)

(73) Assignee: Cagenix, Inc., Memphis, TN (US)

( * ) Notice: Subject to any disclaimer, the term of this patent is extended or adjusted under 35 U.S.C. 154(b) by 0 days.

(21) Appl. No.: 10/391,092

(22) Filed: Mar. 18, 2003

(65) Prior Publication Data

US 2004/0185419 A1   Sep. 23, 2004

(51) Int. Cl.
*A61C 8/00* (2006.01)
(52) U.S. Cl. ........................ 433/173; 433/174
(58) Field of Classification Search .............. 433/173, 433/174, 175
See application file for complete search history.

(56) References Cited

U.S. PATENT DOCUMENTS

| | | | | |
|---|---|---|---|---|
| 4,468,200 | A | * | 8/1984 | Munch ................... 433/174 |
| 4,850,873 | A | * | 7/1989 | Lazzara et al. ............. 433/220 |
| 4,960,381 | A | | 10/1990 | Niznick ..................... 433/174 |
| 4,988,298 | A | | 1/1991 | Lazzara et al. ............. 433/173 |
| 5,030,095 | A | | 7/1991 | Niznick ..................... 433/173 |
| 5,061,181 | A | | 10/1991 | Niznick ..................... 433/174 |
| 5,071,350 | A | | 12/1991 | Niznick ..................... 433/173 |
| 5,205,745 | A | * | 4/1993 | Kamiya et al. ............. 433/173 |
| 5,246,370 | A | * | 9/1993 | Coatoam ................... 433/173 |
| 5,281,140 | A | | 1/1994 | Niznick ..................... 433/172 |
| 5,338,196 | A | | 8/1994 | Beaty et al. ................ 433/172 |
| 5,368,483 | A | * | 11/1994 | Sutter et al. ................ 433/173 |
| 5,431,567 | A | | 7/1995 | Daftary |
| 5,433,606 | A | | 7/1995 | Niznick et al. ............. 433/173 |
| 5,527,182 | A | | 6/1996 | Willoughby ................ 433/172 |
| 5,547,377 | A | | 8/1996 | Daftary ..................... 433/172 |
| 5,564,921 | A | * | 10/1996 | Marlin ...................... 433/172 |
| 5,622,500 | A | | 4/1997 | Niznick ..................... 433/173 |
| 5,662,473 | A | | 9/1997 | Rassoli et al. ............. 433/172 |
| 5,725,375 | A | | 3/1998 | Rogers ..................... 433/172 |
| 5,759,034 | A | * | 6/1998 | Daftary ..................... 433/173 |
| 5,772,437 | A | | 6/1998 | Rangert et al. ............. 433/174 |
| 5,779,480 | A | * | 7/1998 | Groll et al. ................ 433/173 |
| 5,785,525 | A | * | 7/1998 | Weissman .................. 433/174 |
| 5,810,592 | A | * | 9/1998 | Daftary ..................... 433/173 |
| D401,694 | S | | 11/1998 | Daftary ..................... D24/155 |
| 5,829,977 | A | | 11/1998 | Rogers ..................... 433/172 |
| 5,873,722 | A | | 2/1999 | Lazzara et al. ............. 433/173 |
| 5,899,697 | A | | 5/1999 | Lazzara et al. ............. 433/173 |
| 5,947,733 | A | | 9/1999 | Sutter et al. ................ 433/173 |
| 5,967,781 | A | | 10/1999 | Gittleman .................. 433/172 |
| 5,967,783 | A | * | 10/1999 | Ura .......................... 433/174 |
| 5,984,680 | A | | 11/1999 | Rogers ..................... 433/173 |
| 6,012,923 | A | | 1/2000 | Bassett et al. ............. 433/172 |
| 6,039,568 | A | * | 3/2000 | Hinds ....................... 433/175 |

(Continued)

OTHER PUBLICATIONS

AltatecBiotechnologies "The Camlog Abutments".

(Continued)

*Primary Examiner*—Ralph A. Lewis
(74) *Attorney, Agent, or Firm*—Butler, Snow, O'Mara, Stevens & Cannada PLLC

(57) ABSTRACT

A unitary dental implant in the form of an elongate member has an upper abutment portion and a lower fixture portion. An axially extending and upwardly facing planar surface is defined between the abutment portion and the fixture portion.

26 Claims, 26 Drawing Sheets

U.S. PATENT DOCUMENTS

| | | |
|---|---|---|
| 6,120,292 A | 9/2000 | Buser et al. .................. 433/173 |
| 6,120,293 A | 9/2000 | Lazzara et al. .............. 433/173 |
| 6,129,548 A | 10/2000 | Lazzara et al. .............. 433/172 |
| 6,155,828 A | 12/2000 | Lazzara et al. .............. 433/173 |
| 6,164,969 A * | 12/2000 | Dinkelacker ................. 433/173 |
| 6,174,166 B1 | 1/2001 | Jorneus ....................... 433/172 |
| 6,227,856 B1 | 5/2001 | Beaty et al. ................. 433/172 |
| 6,244,867 B1 | 6/2001 | Aravena et al. ............. 433/172 |
| 6,250,922 B1 | 6/2001 | Bassett et al. .............. 433/172 |
| 6,287,117 B1 | 9/2001 | Niznick ....................... 433/173 |
| 6,358,050 B1 | 3/2002 | Bergstrom et al. ........... 433/173 |
| D455,833 S | 4/2002 | Daftary ....................... D24/155 |
| 6,386,876 B1 | 5/2002 | Lee .............................. 433/173 |
| 6,394,806 B1 | 5/2002 | Kumar ......................... 433/173 |
| 6,431,866 B2 | 8/2002 | Hurson ........................ 433/172 |
| 6,431,867 B1 | 8/2002 | Gittelson et al. ............ 433/173 |
| 6,474,991 B1 | 11/2002 | Hansson ...................... 433/173 |
| D470,939 S | 2/2003 | Daftary ....................... D24/156 |
| 6,854,972 B1 | 2/2005 | Elian |

OTHER PUBLICATIONS

"Aesthetic Soft Tissue Integration and Optimized Emergence Profile: Provisionalization and Customized Impression Coping" Practical Periodontics & Aesthetic Dentistry 1999; 11(3); 305-314.

"Anterior Implant-Supported Reconstructions: A Surgical Challenge" Practical Periodontics & Aesthetic Dentistry 1999; 11(5); 551-558.

"Recession of the soft tissue margin at oral implants" Bengazi, et al. Clinical Oral Implants Research, 7: 303-310.

Managing the Soft Tissue Margin: The Key to Implant Aesthetics Lazzara Practical Periodontics and Aesthetic Dentistry, vol. 5, Jun./Jul. 1993 (8 pages).

* cited by examiner

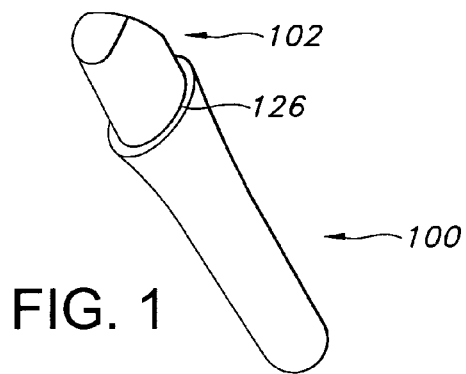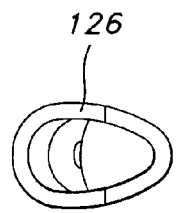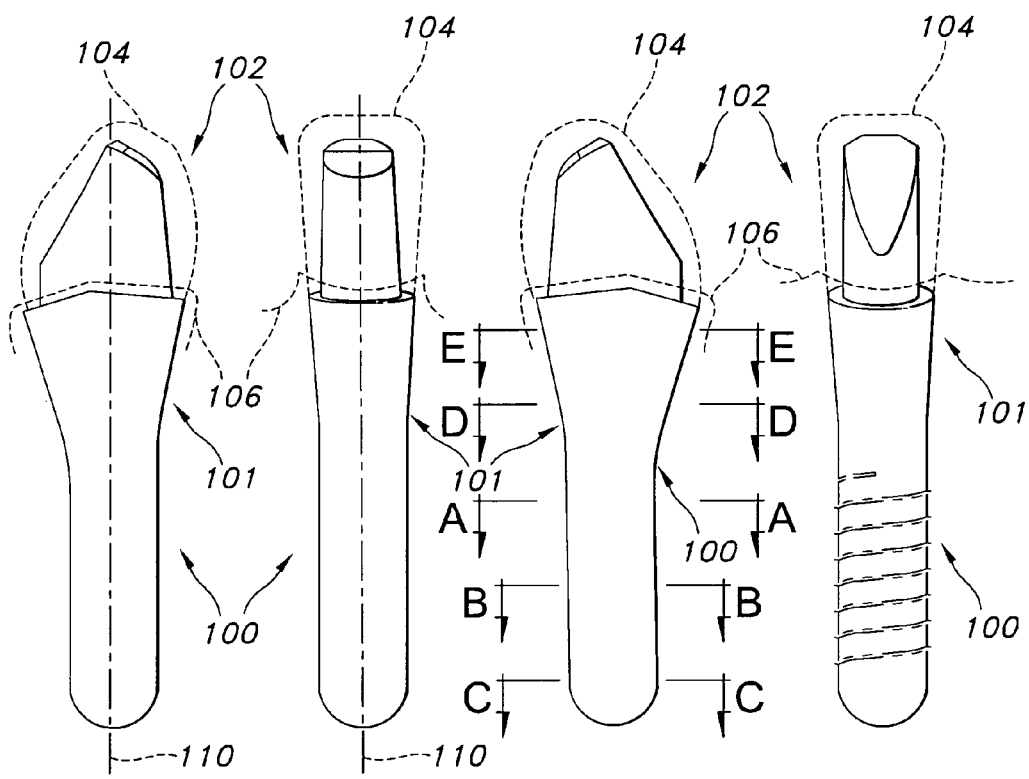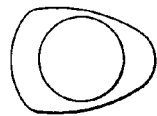
FIG. 1  FIG. 2
FIG. 3  FIG. 4  FIG. 5  FIG. 6
FIG. 7

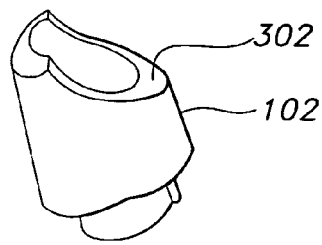
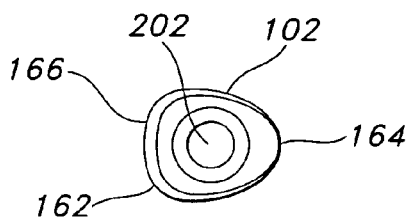
FIG. 60  FIG. 61
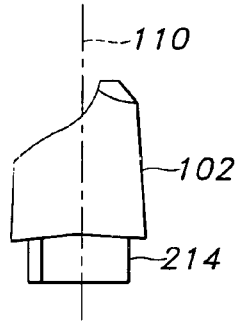 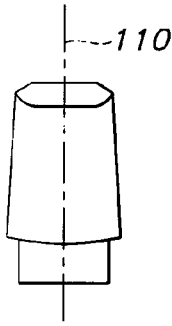 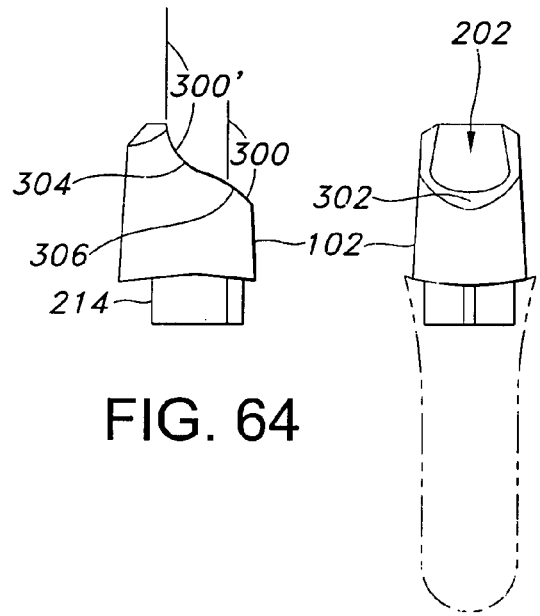
FIG. 62   FIG. 63   FIG. 64
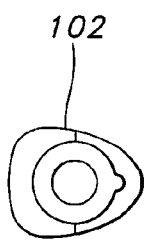
FIG. 65
FIG. 66

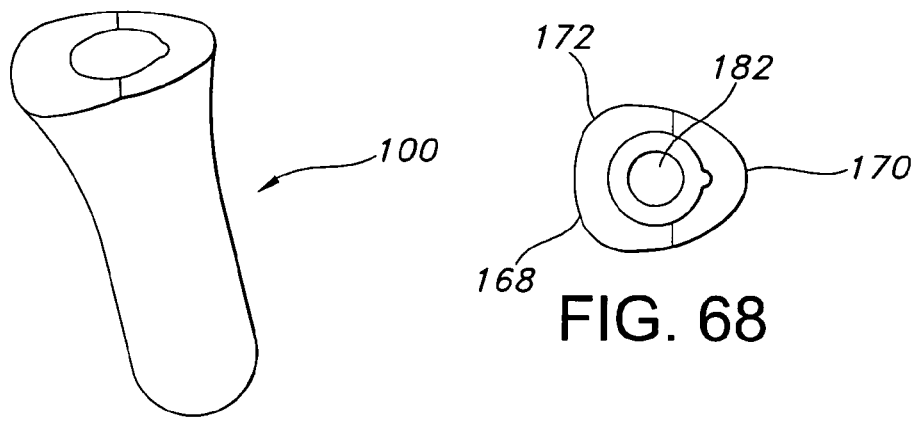
FIG. 67
FIG. 68
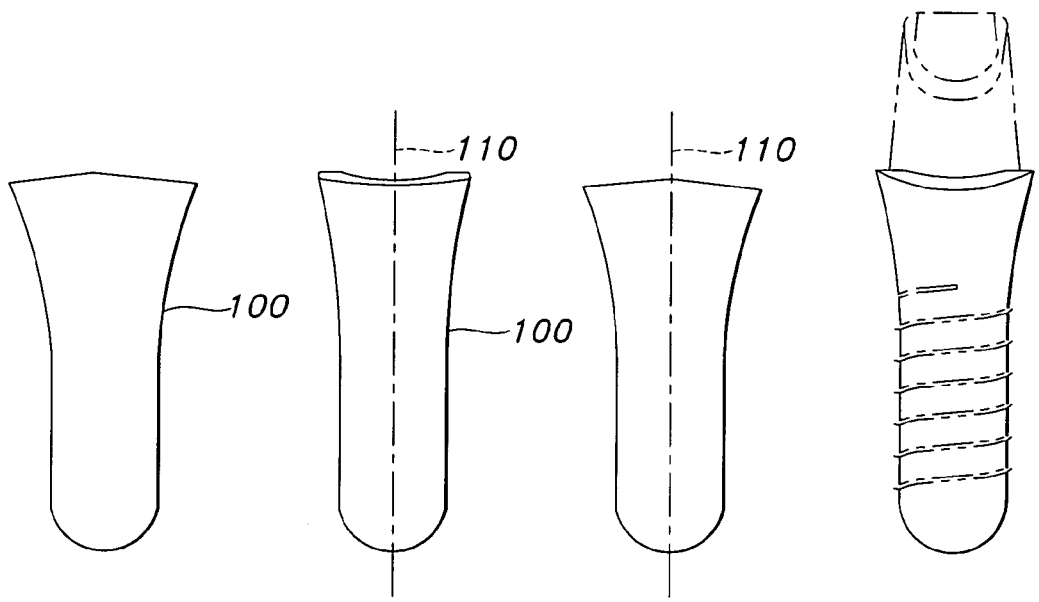
FIG. 69　FIG. 70　FIG. 71　FIG. 72
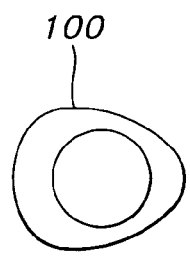
FIG. 73

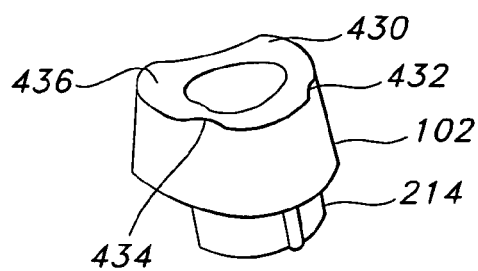
FIG. 102
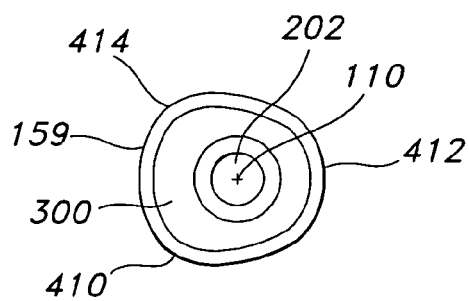
FIG. 103
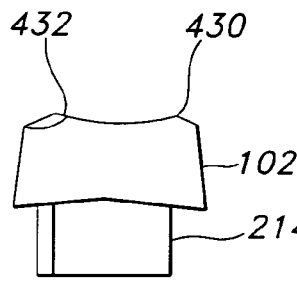
FIG. 104 FIG. 105 FIG. 106
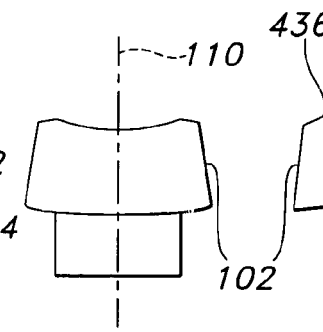
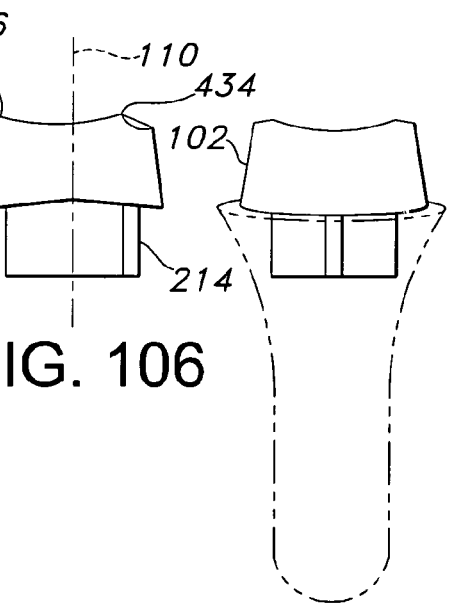
FIG. 107
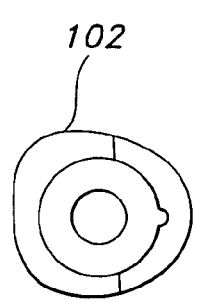
FIG. 108

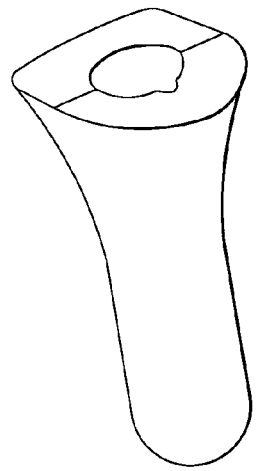
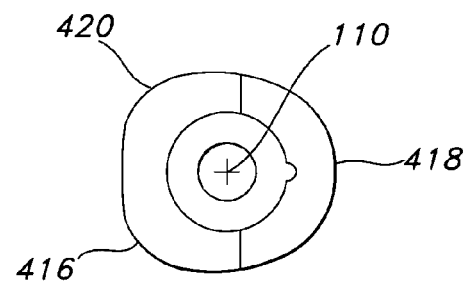
FIG. 109  FIG. 110
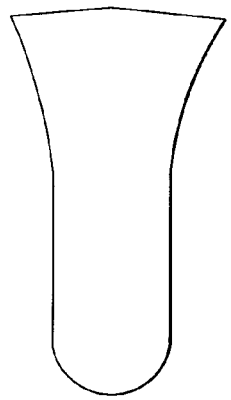 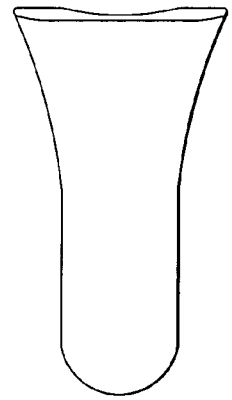 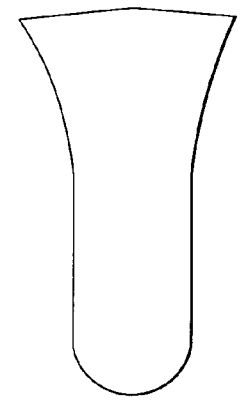 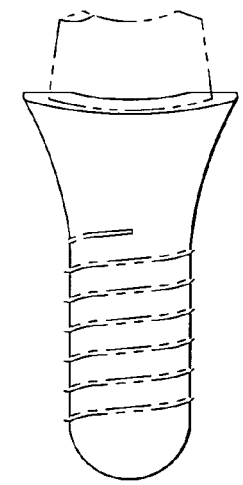
FIG. 111  FIG. 112  FIG. 113  FIG. 114
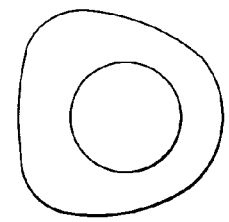
FIG. 115

LOBED DENTAL IMPLANT

FIELD OF THE INVENTION

This invention relates to unitary dental implants.

BACKGROUND OF THE INVENTION

Dental implants are used as replacements for missing teeth. Implants are typically in the form of a fixture that is coupled to an abutment. The fixture portion of a dental implant is that portion which extends into the maxilla or mandible, where it is anchored in a bone in the maxilla or mandible. The fixture typically includes a top portion that extends out of the maxilla or mandible and provides an anchoring point for an abutment. The abutment portion of a dental implant is the portion that is fixed to the fixture and extends above the gingiva. It has an upper surface that is configured to receive and support a crown.

There are several common problems with such two piece dental implants. First, the bone into which they are inserted often does not bond (e.g. integrate) well with the implant, or, if bonded, degrades causing the implant to loosen over time.

Microgaps between the fixture and the abutment are one cause of this loss of bone. The fixture is often positioned within the maxilla or mandible such that its upper surface is below the gingiva. When an abutment is fixed to the fixture, there is a tiny gap between the abutment and the fixture that is at least partially disposed beneath the gingiva. This microgap becomes a haven or reservoir for oral bacteria. By cultivating oral bacteria so close to the fixture/bone junction itself, the gingiva may become irritated or infected, and the bond between the fixture and the maxilla or mandible weakened. Loosening may also be caused by the poor distribution of forces from the implant to the maxilla or mandible. If the load is concentrated on a particular portion of the maxilla or mandible, this stress concentration may cause the bond between fixture and maxilla or mandible to weaken. Stress concentrations are typically caused by improper fixture design or positioning, or a fixture that is not shaped to distribute the tooth load relatively evenly.

Another problem often encountered with implants is the failure of the crown that is attached to the abutment. Large loads placed on the crown when chewing cause the crown to fatigue and ultimately to fracture. These large loads can also weaken the cement that bonds the crown to the abutment if the crown-to-abutment joint design unduly concentrates the load.

What is needed, therefore, is an improved dental implant that reduces the chance of infection and fixture loosening. It is an object of this invention to provide such a dental implant that alleviates these problems in one or more of the illustrated embodiments

SUMMARY OF THE INVENTION

In accordance with a first embodiment of the invention, a dental implant in the form of an elongate body is provided, the implant having a longitudinal axis, the implant including a generally cylindrical upper abutment portion having an upper end, a lower end, and an outer wall extending between the upper and lower ends and generally tapering inwardly toward the longitudinal axis; and a generally cylindrical and elongate lower fixture portion having a lower end and an upper end, wherein said lower end is configured to be inserted into a maxilla or mandible; and an inwardly flaring upper fixture portion having a lower end and an upper end, said lower end of said fixture portion being formed integral with the upper end of the lower fixture portion, and said upper end of said upper fixture portion being coupled to the lower end of said upper abutment portion; wherein the upper end of the upper fixture portion includes a generally axially extending and upwardly facing planar surface that is revolved substantially tangentially about the periphery of the implant.

BRIEF DESCRIPTION OF THE DRAWINGS

FIGS. 1–7 are perspective, top, right-side, front, left-side, rear and bottom views of a unitary right central mandibular incisor implant.

FIGS. 32–45 illustrate the upper portion and the lower portion of a two-piece implant intended to be used in place of an upper cuspid having the same mating construction as that described above with regard to FIGS. 25–31 wherein FIGS. 32–38 are perspective, top, right-side, front, left-side, rear, and bottom views of the upper portion of the implant and FIGS. 39–45 are perspective, top, right-side, front, left-side, rear, and bottom views of the lower portion into which the upper portion is inserted.

FIGS. 46–59 illustrate the upper and lower portion of a two-piece implant intended for use as a lower cuspid in which FIGS. 46–52 are perspective, top, right-side, front, left-side, rear, and bottom views of the upper portion of the implant and further wherein FIGS. 53–59 are perspective, top, right-side, front, left-side, rear and bottom views of the lower portion of the implant.

FIGS. 60–73 illustrate the upper and lower portions of a two-piece implant intended for use as a first lower pre-molar, wherein FIGS. 60–66 are perspective, top, right-side, front, left-side, rear and bottom views of the upper portion of the implant and FIGS. 67–73 are perspective, top, right-side, front, left-side, rear and bottom views of the lower portion of the implant.

FIGS. 74–87 illustrate an alternative two-piece implant intended for use as a first upper pre-molar implant, in which FIGS. 74–80 illustrate perspective, top, right-side, front, left-side, rear and bottom views of the upper portion of the implant and FIGS. 81–87 illustrate perspective, top, right-side, front, left-side, rear, and bottom views of the lower portion of the implant.

FIGS. 88–101 illustrate the upper and lower portions of a two-piece implant intended to replace a lower molar, in which FIGS. 88–94 illustrate perspective, top, right-side, front, left-side, rear, and bottom views of the upper portion of the implant and FIGS. 95–101 illustrate perspective, top, right-side, front, left-side, rear, and bottom views of the lower portion of the implant.

FIGS. 102–115 illustrate an alternative two-piece implant intended to be used as an upper molar, wherein FIGS. 102–108 are perspective, top, right-side, front, left-side, rear, and bottom views of the upper portion of the implant and FIGS. 109–115 illustrate perspective, top, right-side, front, left-side, rear and bottom views of the lower portion of the implant.

DETAILED DESCRIPTION OF THE INVENTION

Figure 8:
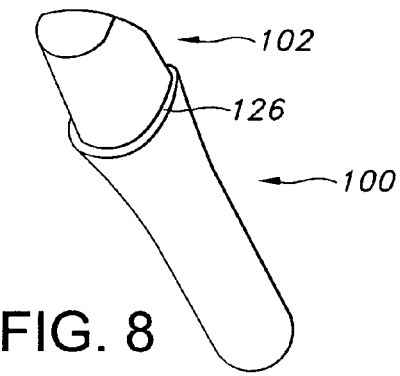
FIGS. 8–14 are perspective, top, right-side, front, left-side, rear and bottom views of a unitary right lateral maxillar incisor implant.

In the discussion below, the Applicants describe a dental implant that is inserted into prepared holes in a mandible or maxilla. To describe several features of the implant, the Applicants use several terms that are here defined or described. "Up" used herein with reference to teeth, implants, fixtures, or abutments, refers to the direction generally parallel to the longitudinal axis of the implant or tooth and extending away from the bone in which it is intended to be implanted. "Down" the direction opposite to "up". "Side", as used with reference to teeth, implants, fixtures, or abutments, refers to the portions of the tooth or implant facing the adjacent teeth or implants when the implant is embedded in the mandible or maxilla. The side surfaces of teeth or implants directly face the adjacent teeth or implants. "Sides" can be either mesial or distal depending upon whether they face toward the dental mid-line or away from the dental mid-line, respectively. "Front" used with reference to a tooth or implant refers to that portion that faces outward away from the maxilla or mandible and often referred to as facial. "Rear" used with reference to a tooth or implant refers to that portion of the tooth or implant that faces the inside of the mouth and often referred to as lingual.

The term "CEJ" or "cement-enamel junction", is the line on a tooth defined by the junction of the enameled upper portion and the cementum of the root. It extends around the surface of the tooth generally perpendicular to the longitudinal axis of the tooth and is generally oval in shape. Since the upper portion of a tooth is covered with enamel, the CEJ typically extends around the outer surface of the tooth at the lowest extent of the enamel. If the tooth is eroded, however, the cementum and enamel may not be in contact and therefore the location of the CEJ may be unclear.

The term "CRJ" or "coronal-root junction" refers to the junction between the coronal portion and the root portion of a tooth. It extends around each tooth in a generally oval shape, and is a little higher on the sides of the tooth than on the front or back of the tooth.

A "facial CRJ line" (also "frontal CRJ line") refers to an imaginary line extending across the face of a mandible or maxilla that passes through the front and lowermost portion of the CRJ of each tooth or implant in the mandible or maxilla. Since the mandible and maxilla each have a row of teeth, there are two facial CRJ lines—one wrapping around the outside of maxilla and one wrapping around the outside of the mandible.

A "lingual CRJ line" (also "rear CRJ line") refers to an imaginary line extending across the face of a maxilla or mandible that passes through the rear and lowermost portion of the CRJ of each tooth or implant in the maxilla or mandible. Since the maxilla and mandible each have a row of teeth, there are two lingual CRJ lines—one extending along the inside of the maxilla and one extending along the inside of the mandible.

The "center" a two dimensional shape, such as cross-sections of the various implants described herein, shall mean the location on that two-dimensional body where the first moment of area equals zero.

The "mirror plane" that term is used herein is a plane that extends vertically through the implant from top to bottom, and extending front-to-back from the lingual side to the facial side of the implant. Each illustrated implant has a mirror plane.

The description below is of the dental implants that in whole or in part embody the invention described in the claims following this detailed description. In the discussion below, we explain several features and benefits of the dental implants—features and benefits that may or may not be incorporated in the device or methods described in the following claims.

The implants illustrated and described herein are all configured for use on the right side of the mandible and maxilla. The claims are intended to cover not only implants on the right side, but those on the left side as well. Non-illustrated implants for the left side of the mandible and maxilla would be identical in construction to those on the right side, but exist in mirror image form, mirrored about the mirror plane of each implant. The features, capabilities and construction of each implant on the left side of the mouth (being of identical mirrored construction to those on the right side) are identical to the corresponding implant on the right side of the mouth.

FIGS. 1–7 illustrate a dental implant. The implant is a generally elongate member, with a lower portion or fixture 100 that is configured to be embedded or implanted in a maxilla or mandible, and an upper portion or abutment 102 that extends out of the maxilla or mandible and provides a structure on which a dental prosthesis 104 such as a crown, (colloquially called a "cap" and illustrated in FIGS. 3–6), bridge or framework can be attached.

In the embodiment shown here, the crown 104 (which is illustrated as a dashed line) surrounds the upper portion of the implant, providing a smooth outer surface to simulate a natural tooth. The crown 104 extends above the marginal gingiva 106 (dashed) and preferably slightly below the marginal gingiva.

Dental implants are generally provided either in one or in two pieces. By "one piece," mean that the implant is a single integral body that is made to be implanted in a maxilla or mandible as a single unit, with an upper portion extending upward away from an out of the gingiva.

Figure 25A:
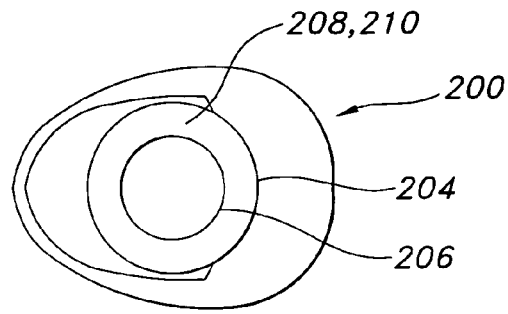
FIGS. 25A–25D illustrate top, side, rear and bottom views of an alternative upper abutment portion of the implant that can be employed together with an alternative form of the lower portion of the implant shown in FIGS. 26A–26C.
Figure 25B:
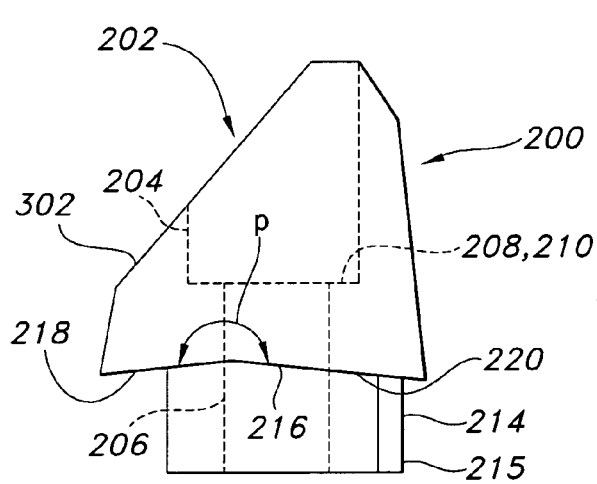
Figure 25D:
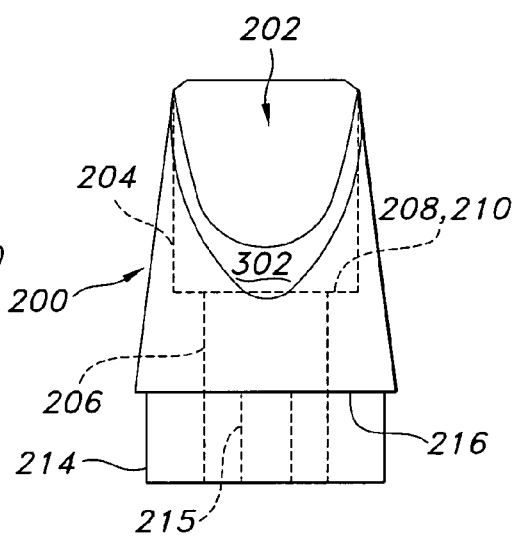
Figure 25C:
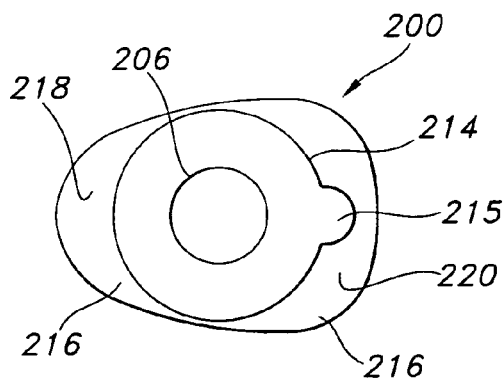

A two-piece implant, such as those shown in FIGS. 25A et. seq. is made of two portions, the upper portion being generally referred to as the abutment and the lower portion being generally referred to as the fixture. In a two-piece implant, the abutment and fixture are coupled together, typically by a threaded fastener, and typically after the fixture has been implanted.

A "fixture" includes at least that portion of a dental implant that is inserted into a maxilla or mandible, or otherwise embedded in bone when in use. An "abutment" includes at least that portion of a dental implant that is configured to be coupled to and support a crown. Of course, there are combined fixtures and abutment arrangements in which the fixture and abutment are formed as a single unit. Examples include the one-piece implants illustrated in FIGS. 1–24. Thus, the terms "abutment" and "fixture" should not be interpreted as requiring a single piece dental implant.

The implant of FIGS. 1–7 is a single piece implant, having an integrated abutment and fixture. It is intended for use as a lower central and lateral incisor. A similar single piece implant can be seen in FIGS. 8–14. It is intended for use as an upper lateral incisor. The description herein regarding the implant of FIGS. 1–7 applies equally to the implant of FIGS. 8–14 except where specifically noted as being applicable only to the implant of FIGS. 1–7 or the implant of FIGS. 8–14.

Figure 15:
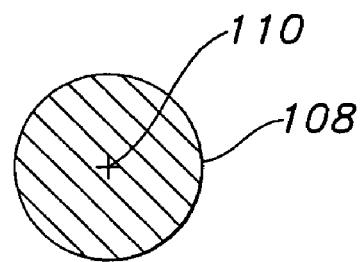
FIG. 15 is a cross-section of both of the implants of FIGS. 1–14 at any of cross-sections A—A, B—B, and C—C.
Figure 16:
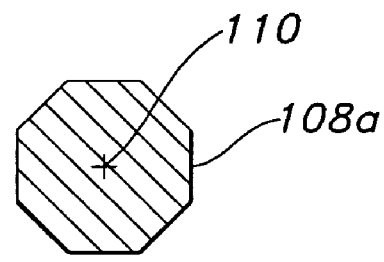
FIG. 16 is an alternative cross-section of any of the implants of FIGS. 1–14 showing a faceted outer surface and taking at sections A—A, B—B, and C—C.

FIG. 15 illustrates cross-sections of the fixtures or lower portions 100 of the implants FIGS. 1–15 taken at cutting lines A—A, B—B, and C—C. These sections are sections through the lower portion 100 of the fixture. The preferred cross-sectional shape 108 as shown in FIG. 15 is circular. Each section in the lower portion of the fixture preferably has the same diameter or the same cross-sectional area. The lower section of the fixture and between cutting lines A—A, B—B, and C—C can have an irregular cross section, however, such as an oval or a polygon. The polygonal shape can be regular or irregular. The polygonal shape can have radiused corners. The polygon can be an convex or concavo-convex polygon. FIG. 16 illustrates a regular convex polygon and cross-section 108a having ten sides. The number of sides is not critical, however, although a range of between 6 and 15 are preferred.

There are advantages to using a fixture with a polygonal lower portion: when a fixture having a polygonal outer surface is inserted into a hole drilled into maxilla or mandible to receive the fixture, the gaps between the outer surface of the polygon and the circular drilled hole in which the fixture is inserted can be filled with a bone growth enhancer, autograft, allograft, or cement, for example. If the material is cement, it may help bond the fixture to the bone in which it is inserted. If the material is a bone growth enhancer, it may encourage bone growth between the fixture and the bone in which it is inserted, thereby providing more rapid healing and a better bond between the fixture and the bone in which it is inserted. Alternatively, the hole may be made by or profiled by an osteotome which preferably has an outer profile similar to the outer surface of the fixture. In this alternative method, a drill may be used to make the initial hole and the hole may then be expanded and profiled by inserting the osteotome straight down into the hole.

The implants of FIGS. 1–14 have a longitudinal axis 110 that extends generally up-and-down through the length of the fixture (or lower portion 100) and through the abutment (or upper portion 102) as well. This axis is defined as a line as close to the center of mass of the lower portion of the fixture as possible. Since, in the preferred embodiments shown here, the cross-sections A—A, B—B and C—C are circular, the longitudinal axis 110 goes through the center of the circular cross-sections. Were the cross-sections irregular, the longitudinal axis would pass through each cross section as close as possible to the a real center of the cross sections as possible.

One can see from FIGS. 15 and 16 that the longitudinal axis 110 goes through the center of each cross section. This indicates that in the preferred embodiment, the lower portion 100 is not bent or curved, but is substantially straight (although the outer surface may taper in the shape of a flaring horn) along the length of the longitudinal axis such that the longitudinal axis extends through the center of all the cross-sections of the lower portion of the fixture 100.

Figure 17:
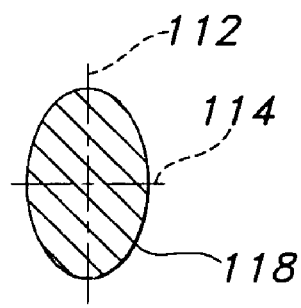
FIG. 17 is a cross-section of either of the implants of FIGS. 1–14 taken at section line D—D.
Figure 18:
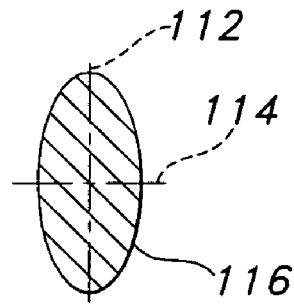
FIG. 18 is a cross-section of any of the implants of FIGS. 1–14 taken at section line E—E.

FIGS. 17 and 18 are cross sections of the upper portion of the fixture 100. Note that the cross-sections are preferably not circular but extend irregularly, being narrower about one axis 112, than about axis 114. The cross-sections of FIGS. 17 and 18 have the general cross-sectional shape of an ellipse. They are also preferably slightly flattened at one end of the major axis 112 to more accurately represent the profile of an incisor. Elliptical cross-section 116 (FIG. 18), the upper cross section E—E of FIG. 5 is larger in area and has a more distinct elliptical shape than elliptical cross-section 118.

If one compares the lower circular cross-section 108 (i.e., A—A, B—B, and C—C) with elliptical cross-sections 118 and 116, it is clear that the higher one moves up the fixture, the more elliptical and less circular the fixture becomes. Thus, the elliptical cross-section 118 shown in FIG. 17 is more elliptical than the circular cross-section 108 shown in FIG. 15 and the elliptical cross-section 116 shown in FIG. 18 is more elliptical than the elliptical cross-section 118 shown in FIG. 17.

The more elliptical a cross-section of an ellipse is, the greater the major/minor axis length ratio of that ellipse as compared to another ellipse. For example, the major/minor axis length ratio of the ellipse 116 of FIG. 18 is greater than the major/minor axis ratio of the ellipse 118 of FIG. 17, which in turn is greater than the major/minor axis ratio of the circle of FIG. 15. The ratio of FIG. 15 is unity, since the cross-section shown in FIG. 15 is a circle.

Note that the major/minor axis ratio preferably (and therefore pictured here as) ratio of FIG. 17 (preferably 1.05–1.25) is between that of FIG. 15 (1.000) and FIG. 18 (preferably 1.15–1.30). By providing a gradually increasing ellipticity (i.e. increasing major/minor axis ratio) as one progresses from the lower portion of the fixture to the upper portion of the fixture, the load provided by the abutment can be more equally distributed to the lower portion of the fixture and then to the mandible or maxilla.

One benefit to the increasing outward taper as one approaches the top of the fixture is that it more accurately represents the shape of a tooth at the equivalent height above the jawbone. Incisors, for example, have generally elliptical cross-sections at a height that corresponds to the height of section E—E (FIG. 18).

By shaping the cross-section of the upper portion of the fixture as closely as possible to the cross-section of the real tooth that it replaces, the maxilla or mandible and the abutting mucosal tissue will better surround the implant in a contour that more closely resembles the bone contour of a natural, undamaged when the bone heals.

Furthermore, by helping the bone and tissue contour to regenerate closer to its natural shape, the gingiva which covers the bone will more closely imitate the original gingiva giving the patient a smile that is more regular, lifelike, and symmetric.

If the upper portion 101 of the fixture 100 is circular in cross-section, it is believed that bone will not heal along the natural bone contour. This could make the bone-to-implant junction weaker, and the gingiva more asymmetric and displeasing to the eye. By making the width of the upper portion of the fixture narrower in the interproximal direction, a gap is provided on either side of the fixture that gives the gingiva more room to grow between adjacent teeth or fixtures and to better surround the base of the tooth.

While the upper portion 101 of the fixtures 100 of FIGS. 1–14 preferably has this irregular cross-sectional shape wider in the facial-lingual direction and narrower in the mesial-distal direction (see FIGS. 17 and 18), it should be understood that an irregular shape is not essential. Indeed, any cross-sectional shape, such as the circular and regular polygonal shapes described above as possibilities for the lower portion of the fixture (see FIGS. 15 and 16) are equally useful for the upper portion 101 of the fixture as well.

As we have shown, the lower portion of the fixture 100 is preferably circular and has a constant cross section as one moves up the fixture. The upper portion 101 of fixture 100 has a cross-section that is preferably non-circular and elongate in a fore-and-aft direction. The cross-sections of the upper portion 101 of the fixture 100 are preferably elliptical and preferably increase in cross-sectional area and irregularity (or out-of-roundness) as one moves up the upper portion of the fixture.

The cross-sectional area of each successive cross-section of the upper portion of the fixture preferably increases and makes the fixture surface flare outward. This gives a greater and greater flare angle the farther one goes upward along the upper portion 101 of the fixture 100.

Figure 19A:
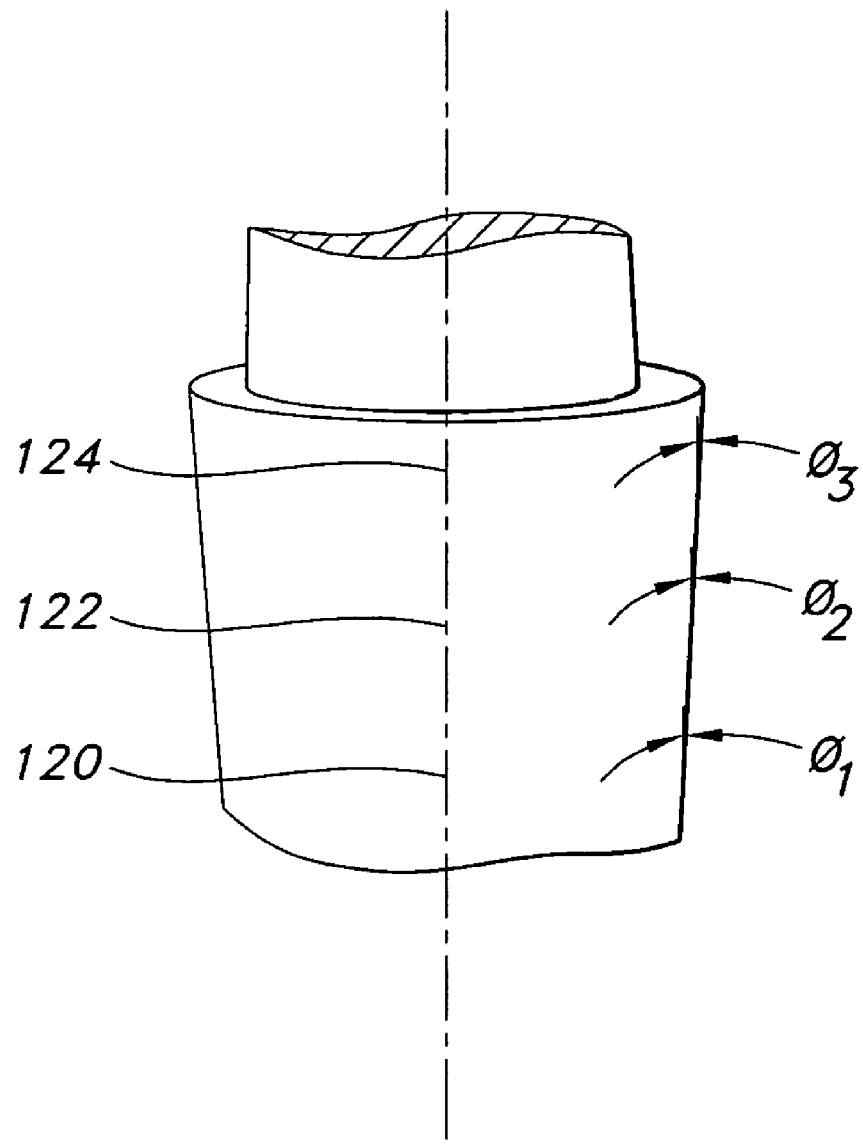
FIG. 19A is a fragmentary front view of any of the implants of the foregoing figures showing how the flare angle measured at the sides of the implant increases as one travels upward along the shaft of the implant.
Figure 19B:
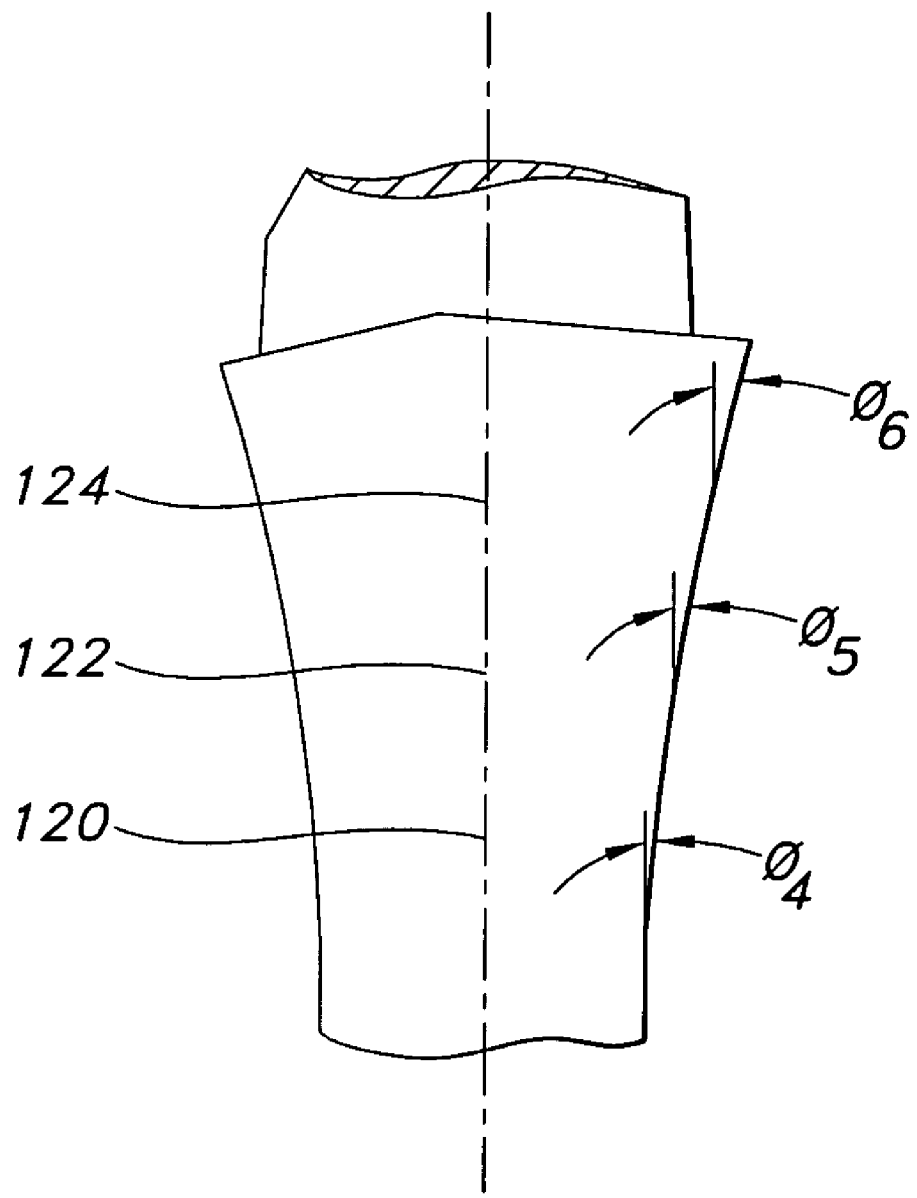
FIG. 19B similarly illustrates how the flare angle increases as one travels upward along the implant as measured on the front side of the implant.
Figure 20:
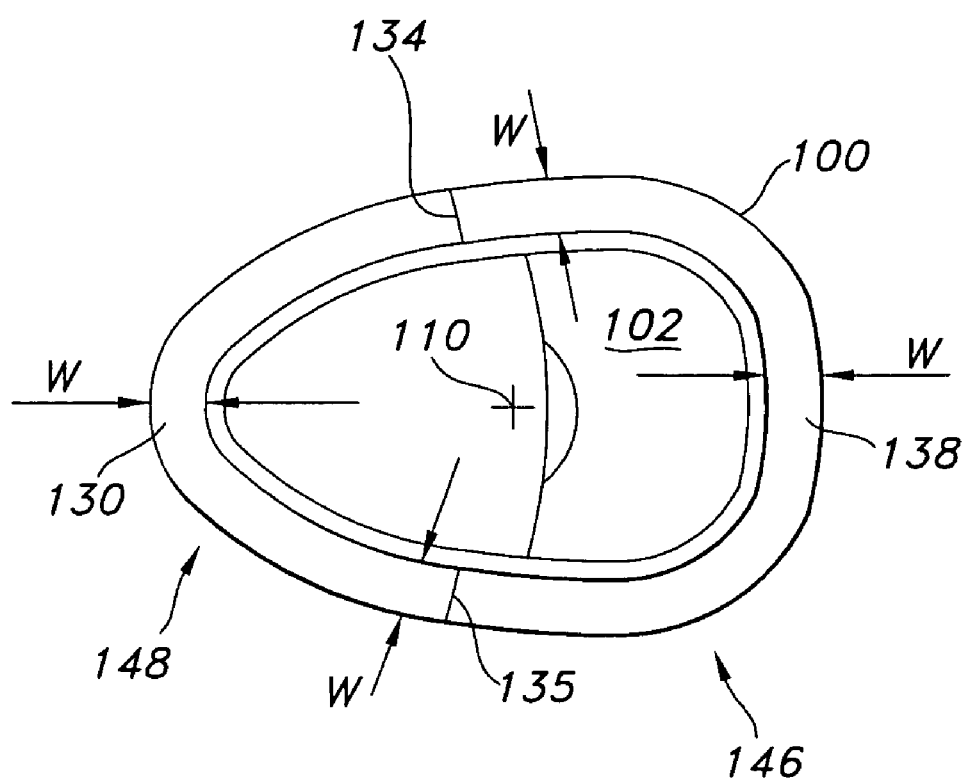
FIG. 20 is a top view of any of the foregoing implants illustrating the narrow band having a Width that extends circumferentially around the entire implant.

By "flare angle" mean the angle between the longitudinal axis of the fixture and a line segment tangent to the surface of the fixture, wherein the line segment tangent lies in the same plane as the longitudinal axis of the fixture. The further up the upper portion of the fixture one goes, the greater the flare angle. As one moves up the fixture, the outer surface or wall of the fixture increases its angle with respect to the longitudinal axis or increasingly flares away from. FIGS. 19A and 19B illustrate this. FIG. 19A is a partial front and FIG. 19B is a partial side view of the implant of FIGURES. 1–7 showing the upper portion of the fixture. In FIG. 19A, the flare angle of the outer surface or wall of the fixture is shown in three (3) locations 120, 122, and 124 along the longitudinal axis, where location 122 is above location 120 and location 124 is above location 122.

The flare angle Ø at position 120 is preferably between 1 and 3 degrees. Traveling up the upper portion 101 of the fixture, the flare angle Ø at position 122 is preferably 2 and 5 degrees. Traveling even further up the upper portion of the fixture, the flare angle Ø at position 124 is preferably between 4 and 8 degrees.

Referring now to FIG. 19B, the flare angle between the front wall of the upper portion of the fixture and the longitudinal axis is illustrated.

The flare angle Ø at location 120 is preferably between 3 and 8 degrees. The flare angle Ø at location 122 along the longitudinal axis is preferably between 6 and 12 degrees. The flare angle Ø at location 124 along the longitudinal axis of the fixture is preferably between 10 and 25 degrees. The flare angles of the back wall of the fixture are similar to those of the front wall at each location 120, 122, and 124 flare angle at the front and back of the fixture is greater than the flare angles at each side of the fixture.

Another preferred characteristic of the fixture is the increasing irregularity of its cross sections as one moves up along the upper portion of the fixture. For example, the cross-section shown in FIG. 15 is regular: a circle. The cross-sections shown in FIGS. 17 and 18 are less regular and more elliptical, with their area distributed farther from the center (or centric) of the area of the lower cross-sections A—A, B—B, C—C (FIGS. 15 and 17).

Another preferred characteristic of the fixture is the increasing normalized second moment of area of each of the fixture's successive cross-sections about the centroid of each said successive cross-section, as one progresses from cross-sections at the bottom of the upper portion of the fixture to and through successive cross-sections near or at the top of the upper portion of the fixture.

The second moment of an area (such as the cross-sections through the fixture) about a centric of that area is the sum over the entire area of each constituent infinitesimal area times the square of the distance of that infinitesimal area from the centroid of the overall area. In this case, the second moment of area is calculated about an axis that passes through the centroid of the cross-sectional area and is parallel with the longitudinal axis of the fixture. A normalized second moment of a (cross-sectional) area is the second moment of that (cross-sectional) area divided by the second moment of a circular disk having the same area as that (cross-sectional) area.

By this definition, the normalized second moment of the cross-sectional area of FIG. 15 is one (1.0) since the actual cross-section of FIG. 15 is a circular disk, and the longitudinal axis passes through the center. The normalized second moment of area of the circular cross-section 108 is the second moment of a circle having the area of cross-section 108 divided by the second moment of a circle of the same area. Since the preferred and illustrated cross-sections A—A, B—B, and C—C are already circles, the numerator and the denominator are the same, and therefore the ratio of second moments is one, regardless of the actual area of the circular cross-section of FIG. 15. By extension (1.0), the normalized second moments of area of the cross-sections of FIGS. 17 and 18 are greater than one (1.0). Furthermore, the normalized second moment of area of the cross-section of FIG. 18 is greater than that of the cross-section of FIG. 17.

By increasing the second moment of area in successive cross-sections of the upper portion of the fixture, loads placed on the abutment can be more effectively distributed and transferred to the bone that surrounds the lower portion of the fixture.

The normalized second moment of area preferably increases as one moves upward through successive cross-sections of the upper portion of the fixture, as explained immediately above. It is also preferable that this increase in normalized second moment is continuous and unbroken as one moves upward through the fixture. By "continuous and unbroken" mean that successive cross-sectional areas of the upper fixture's cross-sections meet the requirement that their normalized second moment (as described above) is greater than the normalized second moment of the cross-section immediately below, and is smaller than that of the cross-section immediately above.

Another preferred characteristic of a possible embodiment of the fixture is that the flare angle of its walls changes at different rates depending upon circumferential position around the longitudinal axis where that flare angle is measured.

FIGS. 19A and 19B show how the outer surface of the fixture flares at four different locations around its periphery at three successively higher longitudinal positions 120, 122, and 124. Note that the flare angle increases at different rates depending upon the location around the periphery or circumference of the fixture. The term "rate of flare" used here means the rate at which the flare angle increases per unit of distance traveled upward along the longitudinal axis of the fixture. In FIG. 19A, the flare angle of the side walls of the upper portion of the fixture, change from Ø 1 equals 2 degrees at location 120 to Ø 2 equals 3.5 degrees at location 122. This gives a rate of increase of the side wall flare angle of 1.5 degrees over the distance traveled from location 120 to location 122. In FIG. 19B, at location 120, the flare angle is Ø 4 equals 4.5 degrees and at location 122, the flare angle is Ø 5 equals 9 degrees. The rate of change of the flare angle as one travels from location 120 to location 122 along the longitudinal axis of the fixture is 9 degrees minus 5.5 degrees or 3.5 degrees. This is greater than the 1.5 degrees increase in flare angle measured along the side wall of the fixture as shown in FIG. 19A. Locations 120, 122 and 124 are spaced equally far apart. Thus, depending on one's position around the periphery of the upper portion of the fixture at a particular position along the longitudinal axis, the flare angle varies and the rate of change of the flare angle (the rate of flare) varies as well.

Figure 9:
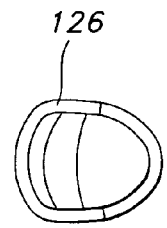
Figure 10:
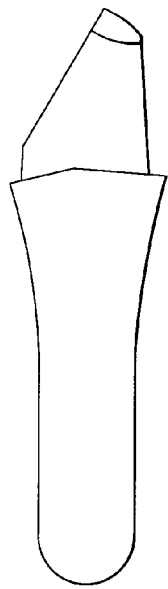
Figure 11:
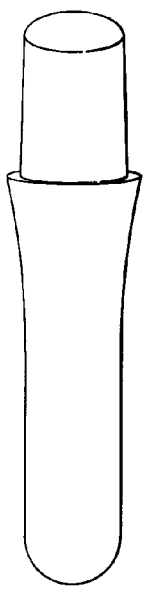
Figure 12:
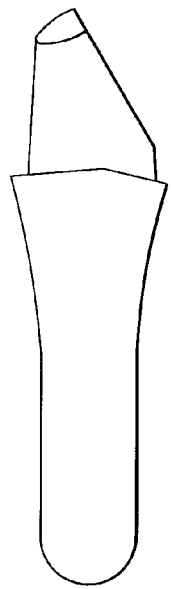
Figure 13:
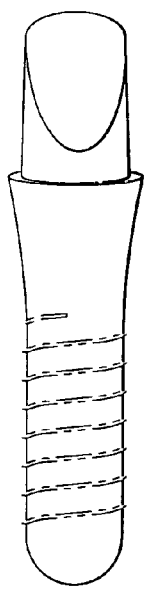
Figure 14:
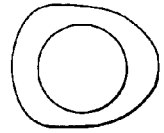

FIGS. 2 and 9 are top views of the fixtures of FIGS. 1–14 showing how the tops of the fixtures preferably extend radially outward away from the base of the abutment, preferably face upward and define a narrow band 126 that extends outward away from the lower portion of the abutment and generally perpendicular to axis 110. This narrow band 126 is preferably not circular in plane view, but instead has an irregular outer profile such as the elliptical profile shown in the cross-sections D—D and E—E of FIGS. 1–14. The width ("W" in FIG. 20) of the narrow bands 126 (i.e. their extent in the radial direction—the directions perpendicular to axis 110) is preferably constant as one travels around the periphery of the fixture and preferably measures between 0.25 mm and 1 mm.

The top of the fixtures intended for different tooth positions along the mandible preferably have different contours, each contour mimicking the contours of the tooth that is being replaced since the shape of the upper portion of the fixture in the mouth may have different contours. The contours of this narrow band preferably vary from implant to implant depending upon the location along the mandibles.

As one follows the band around the circumference of the fixture the path described by band preferable rises and falls—it moves up and down along the longitudinal axis of the implant. By "rising" mean that it moves upward. By "falling", we mean that it moves downward.

Figure 21:
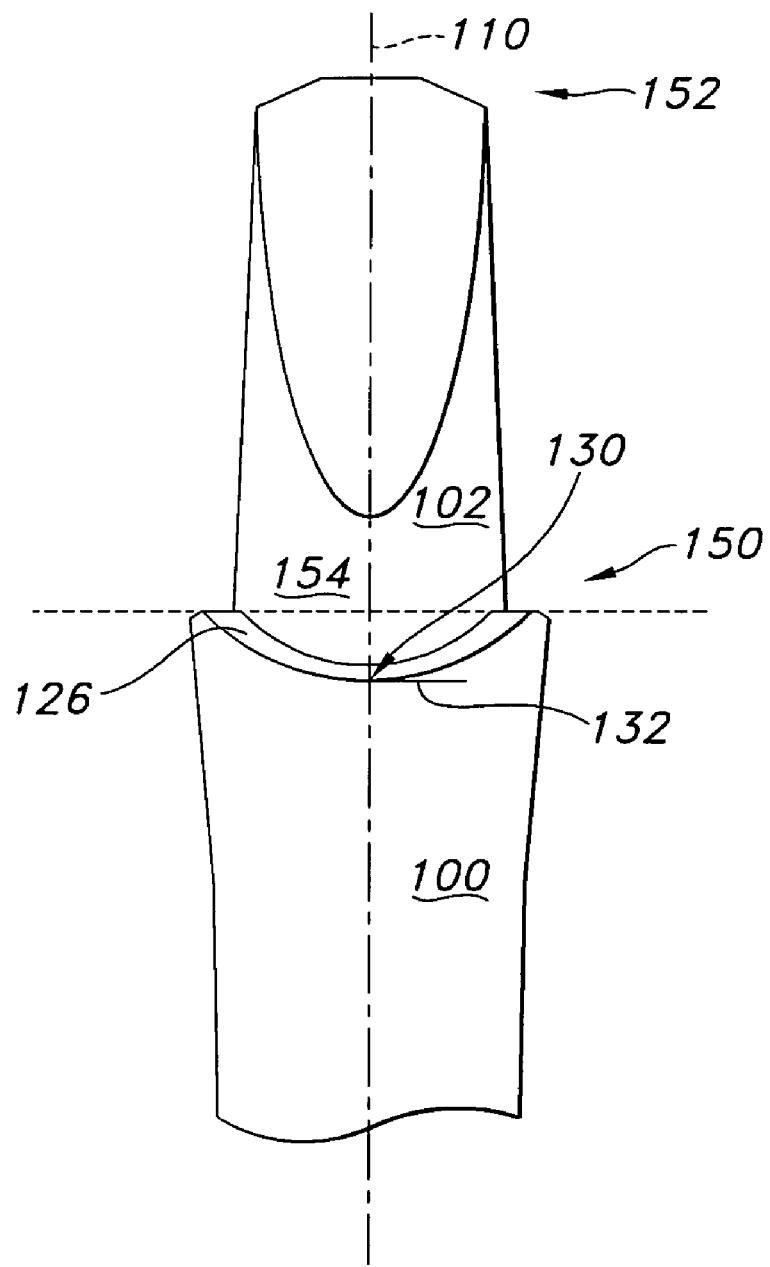
FIG. 21 is a fragmentary rear view of any of the foregoing implants showing a local minima (low point) of the narrow band extending around the implant that is located on the center of the back side of the implant.
Figure 22:
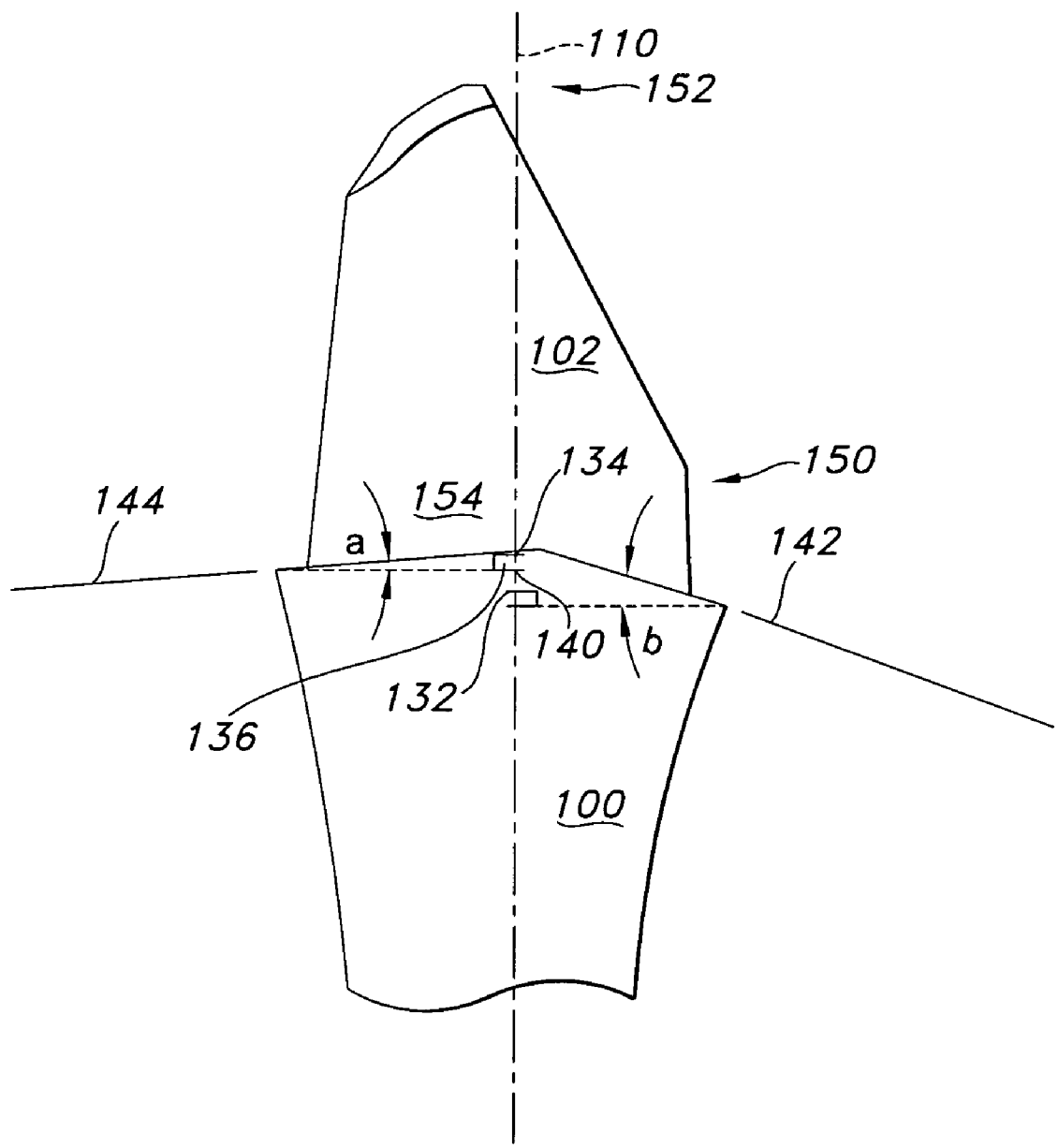
FIG. 22 is a fragmentary side view of any of the foregoing implants showing the local minima at the rear of the implant and a slightly higher local minima at the front of the implant, as well as the two imaginary planes 142 and 144 that define the front portion and rear portion of the narrow band.
Figure 23:
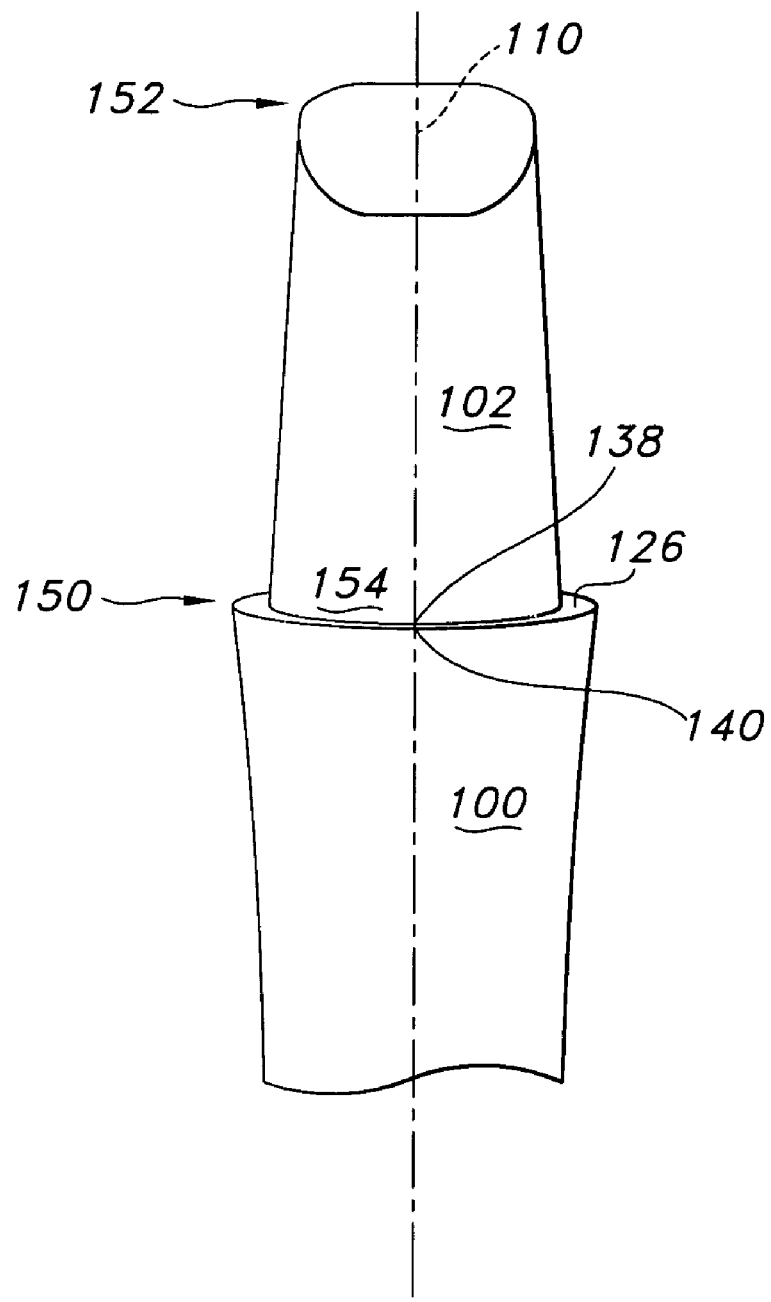
FIG. 23 is a fragmentary front view of any of the foregoing implants showing the local minima at the front center of the implant.

Referring now to the front views of the incisor implant shown in FIGS. 21–23 note how in each case the band falls to a lowest point or minima 130 at the rear of the implant at a position 132 along the implant's longitudinal axis.

In the left side view of the implants, shown in FIG. 22, note how the band rises to a local high point or maxima 134 at a position 136 along the longitudinal axis of the implant. There is a similar maxima 135 on the opposite side of the implant at the same position 136.

In the front view of the incisor implant shown in FIG. 23, note that the band again falls to a second local low point or minima 138 at position 140 along the longitudinal axis at the rear of the implants.

Thus, each implant has two local minima located at the front and the back of the implant, and two local maxima located at both sides of the implants. Looking at the implants in a direction perpendicular to the implant's longitudinal axes, such as the views shown in FIGS. 21–23, one can see a preferred relative relationship of the local minima with respect to the longitudinal axis. Note that the highest points on the band are the two local maxima 134 and 135 located on either side of the band. The front local minima 138 is below the two local maxima 134 and 135 and the rear local minima 130 is below the front local minima 138.

By locating the minima and maxima as shown, the thrust loads of the tooth are more evenly resisted when the crown (see FIGS. 3–6) presses down against the surface of the narrow band.

This rise and fall of the band from maxima to minima to maxima to minima and back to maxima as it extends around the circumference of the implant varies depending upon the intended installed location of the implant, since the loads are different in each location.

The narrow band 126 preferably defines a planar surface or a plurality of intersecting planar surfaces. As best shown in the side view of FIG. 22, the band 126 defines two imaginary planes 142 and 144 that intersect at the upper maxima 134 and 135.

Since the intersecting planes 142 and 144 intersect, they are, by definition, at an angle to one another. They are also preferably at an angle to the longitudinal axis 110. As shown in FIG. 22, the plane 144 defining the front half of the narrow band 126 is preferably at an angle alpha of between 5 and 15 degrees with respect to the longitudinal axis. More preferably it is at an angle of between 7 and 30 degrees.

The above angles are the angles between the plane and the longitudinal axis as it would appear when projected into a view normal to the longitudinal axis, which in this embodiment is the side view.

The other intersecting plane 142 defines the rear half of the narrow band 126 of the incisor implants of FIGS. 1–15. It, too, is preferably at an angle with respect to the longitudinal axis. The angle beta is preferably between 10 and 50 degrees. More preferably it is between 15 and 40 degrees. Even more preferably, it is between 20 and 55 degrees.

The above angles are the angles between the rear plane and the longitudinal axis as it would appear when projected into a view normal to the longitudinal axis, which in this embodiment are the side views.

The abutment or upper portion 102 of the implants of FIGS. 1–14 preferably tapers inwardly (i.e. toward axis 110) from the base as the abutment extends upward away from the fixture. Successive cross-sections of the abutment (by a plane perpendicular to axis 110) get smaller and smaller in area as one moves upward along the longitudinal axis 110 from the base 150 of the abutment 102 to the top 152 of the abutment. See, for example, FIGS. 21–23. The base 150 of the abutment adjacent to the fixture is preferably one continuous curved surface 154 extending circumferentially around the implant. Surface 154 is tapered inwardly toward the longitudinal axis as it moves upward, having a smaller and smaller cross-sectional area.

The base 150 of the abutment where the abutment meets the fixture 100 is preferably disposed radially inward around the entire circumference of the implant. It is this inward spacing of the abutment away from the edge of the top of the fixture that defines the narrow band 126 described in greater detail above.

The base 150 of the abutment preferably has a cross-sectional shape similar to that of the fixture to which it is coupled. For example, the implants of FIGS. 1–14 have fixtures with upper surfaces and cross-sections that are generally flattened ellipses and hence have major and minor axes. The abutments that extend upward from these fixtures have cross-sections similar to the top portions of the fixture to which they are coupled. They also are preferably flattened ellipses.

Another similarity is that the base of the abutment and the top portion of the fixture have the same number of "nodes". A "node", as the term is used here, describes local protrusions of curvilinear shapes (e.g. regions wherein the circumferential periphery of the implant has a reduced radius of curvature or regions where the periphery curves more sharply). A node exists on each flattened ellipse wherever there is a local minima in the radius of curvature. The three nodes (the three local minima) on the flattened ellipse 159 defined by base of the abutment are identified as items 160, 162 and 164. The three nodes on the flattened ellipse 161 defined by the top of the fixture and corresponding in circumferential location to nodes 160, 162 and 164 are 166, 168 and 170. There are as many nodes as there are minimas of the radius of curvature function as one travels around the periphery of the ellipse. These nodes protrude from their respective flattened ellipses, two at the flattened end 172 of the ellipse at one end 174 of the major axis 176, and one at the other end 178 of the ellipse at the other end of the major axis 176.

Figure 24:
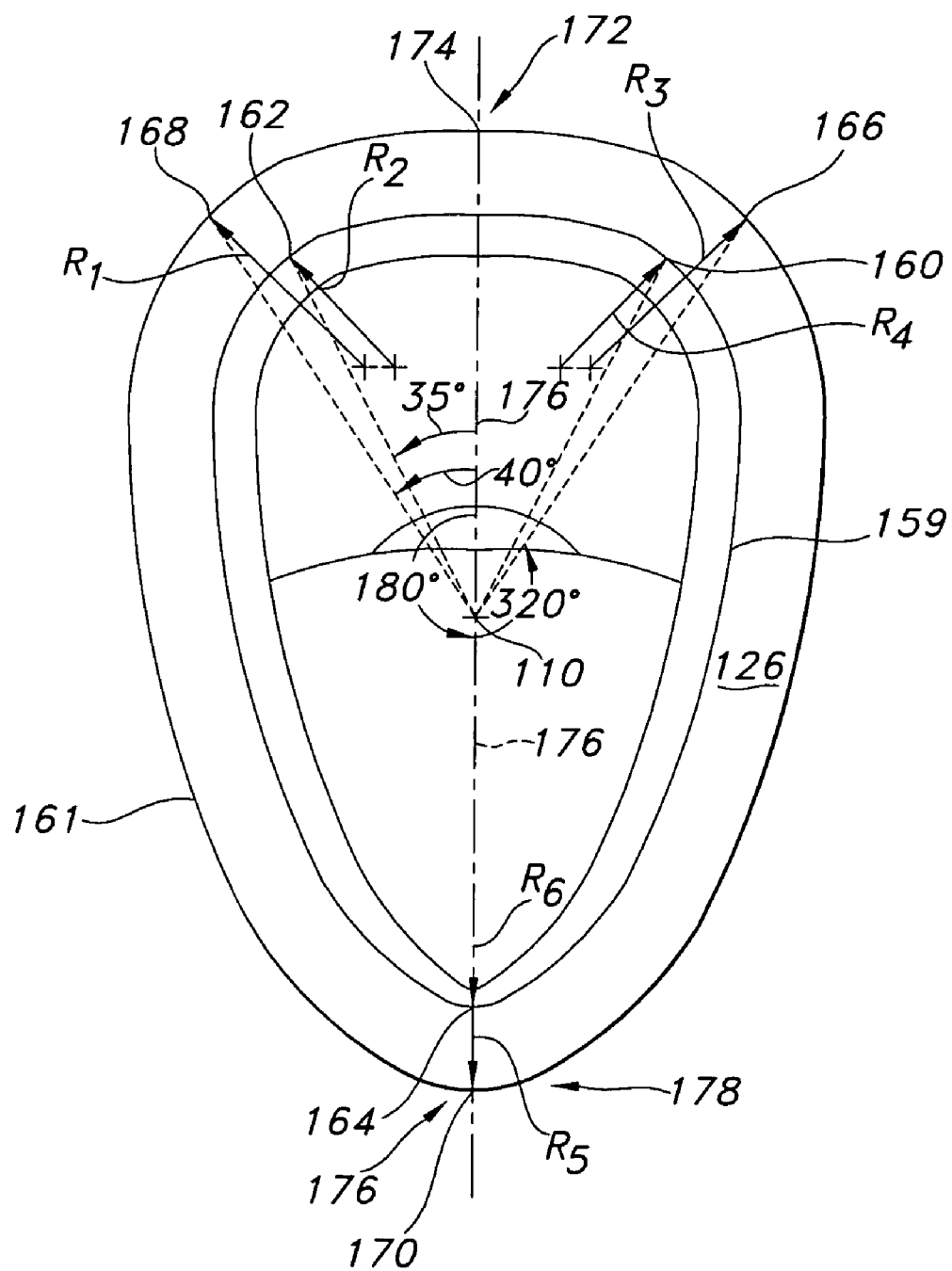
FIG. 24 is a top view of any of the foregoing implants showing the numeral 3-node configuration of both the lower portion of the implant and the upper portion of the implant and also illustrating how each of the three (3) nodes of the upper portion of the implant are disposed immediately adjacent to each of the three (3) nodes of the lower portion of the implant.

Note that the nodes 160, 162 and 164 of the abutment are aligned with corresponding nodes 166, 168 and 170 of the fixture as best seen in FIG. 24. The nodes of each fixture and its corresponding abutment are distributed at the same angular locations around the longitudinal axis of the implant. For the fixture of FIG. 24, node 168 is disposed at 40 degrees, node 170 is disposed at 180 degrees and node 166 is disposed at 320 degrees. For the abutment of FIG. 24, node 162 is disposed at 35 degrees, 164 is disposed at 180 degrees and node 160 is disposed at 325 degrees. These angles are measured with respect to a plane extending fore-and-aft and passing through longitudinal axis 110 of the implant.

FIGS. 3–6 illustrate a preferred orientation of an exemplary implant and its associated prosthesis, shown as crown 104. The implant shown in FIGS. 3–6 shows a preferred coupling of an implant and a crown. Note that the crown 104 extends around and completely covers the free portion of the abutment—e.g. the free outer surface of the abutment extending above the top of the fixture. The lower portion of the crown abuts the fixture, more particularly, the surface of narrow band 126.

The junction created by the lower portion of the crown 104 abutting the narrow band is smooth. The junction is configured to provide a smooth transition from the crown to the fixture, and vice versa.

In the embodiments of FIGS. 1–24, the fixture and the abutment are unitary structures, formed integrally, or formed individually and coupled together to one another before implantation in the maxilla or mandible. For most applications, however, it is desirable to create a multi-piece device having an abutment and fixture that are separate and removably attachable.

In a system using a separately installable fixture a doctor is enabled to implant a fixture, to wait for the fixtures and bone to heal, and to then attach an abutment and crown to the fixture. This delayed assembly permits a fixture to heal before a tooth load is applied. If the entire implant, both fixture and abutment, was installed initially, the patient could only with great difficulty avoid biting down on the implant while the bone heals. Biting forces applied to an implant, especially during the initial fixtures/bone healing phase, can prevent proper healing.

The implants of the following figures (FIGS. 25A et seq.) are all two-piece implants in which the abutment and the fixture are separate and are coupled together after the fixture is embedded in a patient's bone and permitted to heal. In each of the examples of FIGS. 25A et. seq. the abutment and fixture are held together with a screw, and have interengaging binding surfaces that prevent rotation of the abutment with respect to the fixture.

FIGS. 25A–26D show preferred structures that couple the abutment and the fixture.

Figure 26A:
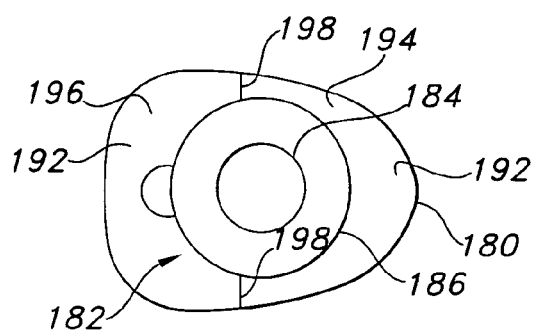
FIGS. 26A–26C are top, side, and rear views of an alternative lower portion of the implant that may be coupled together with the upper portion shown in FIGS. 25A–25D to form a two-piece implant having the identical structure, configuration, arrangement, dimensions, features, and capabilities as the implants described in the foregoing FIGURES with one (1) difference: the implant is made of two pieces coupled together by a cylinder extending downward from the upper portion in FIGS. 25A–25C into the cylindrical recess shown in FIGS. 26A–26C.
Figure 26B:
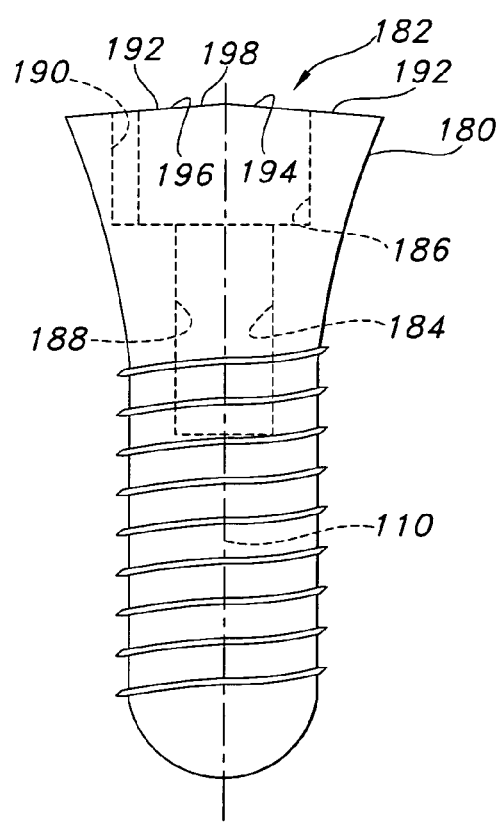
Figure 26C:
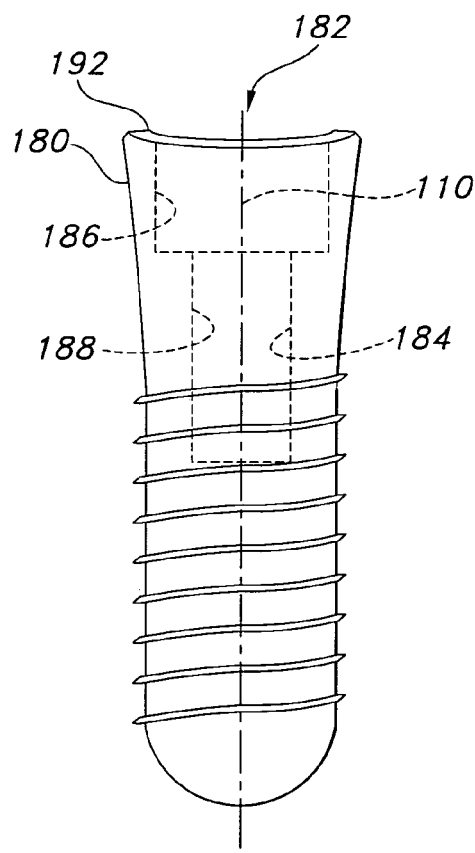

FIGS. 26A–26C show the fixture portion of a two-piece implant in top, side, and rear views, respectively. Exemplary fixture 180 has a hole 182 that extends axially down the middle of the fixture to a depth of between 3 and 10 mm. This hole is a right circular cylinder and has internal threads 184 that are configured to engage a screw (FIG. 26D) that extends through the abutment (FIGS. 25A–25D) into the fixture.

An upper portion 186 of the hole is a right circular cylinder and has a larger diameter than the lower threaded portion 188 of the hole. This upper portion also has an antirotation structure 190, here shown as a half-circle slot that is formed in the wall of the upper portion of the hole 182. This slot defines a surface that interengages with the abutment to prevent the abutment and the fixture from rotating with respect to each other.

Slot 190 is preferably shaped as an arc of circle as viewed from above and as best shown in FIG. 26A. The transition between the slot 190 and the upper portion 186 is preferably rounded or radiused.

The diameter of the upper portion 186 of hole 182 is preferably between 1.2 and 1.7 larger than the diameter of the lower threaded portion 188 of hole 182.

The upper portion 186 of the hole may have a constant diameter, or it may be tapered inward the farther one goes down upper portion 186 to have a smaller and smaller cross-sectional area. If tapered, the taper angle (the angle between the longitudinal axis of the hole and the wall of the upper portion) is preferably between 1 and 10 degrees.

Note that the upper surface 192 of the fixture is generally planar, in the form of two intersecting planes 194 and 196. These planes join together at a line 198 that extends across the top of the fixture from one side to another, dividing the top of the fixture into two portions of generally equal area. By generally equal, we mean that the area of the top surface of the fixture on one side of line 198 is between 0.8 and 1.25 times the size of the area on the other side of the line.

In FIGS. 25A–25D, the abutment 200 has a central hole 202 that extends entirely through the abutment. This hole is slightly larger in diameter than the threads of the screw (FIG. 26D) designed to mate with threaded hole 188 in the fixture.

The upper portion 204 of central hole 202 has a larger diameter than the lower portion 206 of central hole 202. The bottom 208 of the upper portion 204 defines a planar surface 210 that is configured to receive and support the head 203 of the screw 205 (FIG. 26D) that holds the abutment and fixture together.

A cylinder 214 extends downward from the bottom surface 216 of the abutment. This cylinder is configured to fit inside the upper portion 186 of the hole 182 in the fixture. The cylinder 214 is preferably a right circular cylinder, although it may have a taper matching that of the upper portion of the hole in the fixture. Cylinder 214 includes an arcuate projection 215 generally the same in size and orientation as the arcuate slot 190 in the fixture.

Figure 26D:
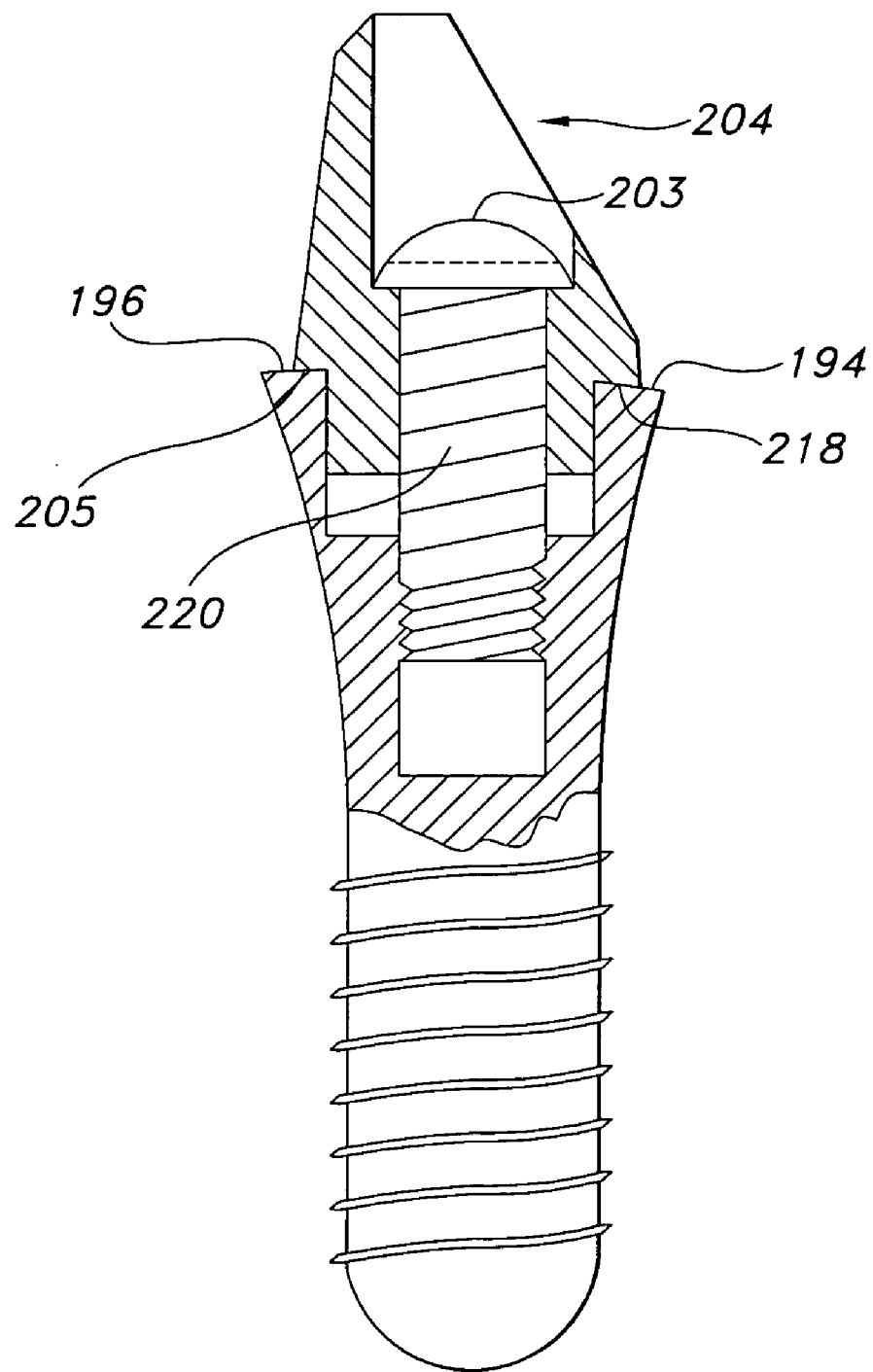
FIG. 26D is a partial cross-sectional left side view of the implant formed by coupling the implant upper portion or abutment of FIG. 25A–25D and the implant lower portion illustrated in FIGS. 26A–26C in which a cylindrical portion of the upper portion extending downward therefrom is received in a matching cylindrical hole in the top of the lower portion shown in FIGS. 26A–26C held together by a screw recessed into the top of the upper portion, extending through the upper portion, and threadly engaged with mating internal threads disposed in the upper part of the lower portion of the implant.

FIG. 26D is a partial cross-section of the abutment and fixture of FIGS. 25A–25D and 26A–26C, showing how they are fixed together by screw 205.

Cylinder 214 is inserted into upper portion 186 of hole 182. The head 203 of screw 205 is configured to enter the upper portion 204 of abutment hole 202 and preferably to be received entirely therein such that it does not extend above upper surface 212 of abutment 200.

The lower surface 216 of the abutment 203 from which the cylinder 214 downwardly extends is in the form of two intersecting planes 218 and 220. These planes are preferably at the same angles with respect to one another and with respect to axis 110 as are planes 194, 196, respectively that form the top of the fixture such that when the fixture and abutment are coupled together, plane 218 abuts and is generally coplanar with plane 194 and plane 220 abuts and is generally coplanar with plane 196. Plane 218 and plane 194 are preferably parallel, as are planes 220 and 196. Furthermore, the angle between planes 194 and 196 on the fixture is the same as the angle between planes 218 and 220 on the abutment.

The planes 194 and 196 that define the top of the fixture have a greater overall area than the overall area of planes 218 and 220 that define the bottom of the abutment. When the cylinder extending from the abutment is inserted into the upper portion of the hole in the fixture, the planes 194 and 196 defining the top of the fixture extend radially outward beyond the planes 218 and 220 that define the bottom of the abutment. This portion of planes 194 and 196 extending beyond the bottom of the abutment define a narrow band 126 that extends around the implant.

This narrow band 126 that extends outward from the junction of the abutment and the fixture that is formed by the planar top surface of the fixture preferably has the same characteristics, extent and orientation as the narrow band 126 described as part of the single piece implant of FIGS. 1–24.

There are several alternative fixture and abutment couplings that are also considered beneficial.

For example, rather than having one arcuate projection 215 on the abutment's cylinder that mates with one arcuate slot 190 in the fixture's hole, more may be provided, such as two, three, four, five, six, seven, or even more.

The slot/projection pairs that engage with each other to prevent rotation of the abutment with respect to the fixture are preferably arranged equiangularly about the longitudinal axis of the implant. For example, if there are two such slot/projection pairs, they are preferably disposed at 180 degrees with respect to each other about the longitudinal axis. If there are three, they are preferably located at 120 degrees with respect to each other. If there are four pairs, they are preferably disposed at 90 degrees, and so on.

In another alternative embodiment, rather than having a cylinder projecting downward from the abutment that, in turn, mates with a similarly shaped hole in the fixture, their positions may be reversed: the cylinder may extend upward from the fixture to be received in and engage a hole extending upward into the bottom of the abutment. In this case, the sizes, shapes and orientations of the cylinder and its receiving hole in FIGS. 25A–26D are the same, merely reversed.

Figure 27:
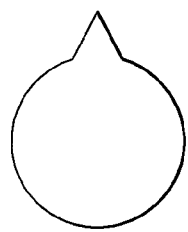
FIG. 27 is an alternative cross-sectional profile of the cylinder of the upper portion of the implants in FIGS. 25A–25D and the cylindrical hole in the lower portion of the implant shown in FIGS. 26A–26C illustrating a triangular sharp-edged protrusion that extends the length of the cylinder in place of the existing protrusion 214 and corresponding recess or slot 190.
Figure 28:
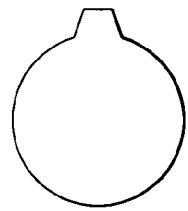
FIG. 28 illustrates an alternative cross-section of the cylinder and cylindrical hole of the foregoing figures showing the protrusion and recess as a three-sided trapezoidal shape.
Figure 29:
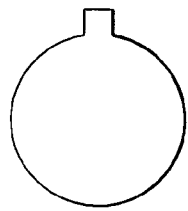
FIG. 29 is yet another alternative profile of the cylinder and cylindrical recess of foregoing figures showing the protrusion and slot as a rectangular (preferably square) shape extending outward from the cylinder.

In yet another alternative embodiment, rather than arcuate slots and projections, the slots and projections may be polygonal, for example triangular (FIG. 27), trapezoidal (FIG. 28), or rectangular (FIG. 29).

Figure 30:
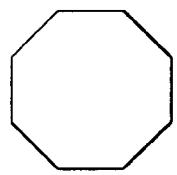
FIG. 30 illustrates an alternative profile of the cylinder and cylindrical hole in the foregoing figures in which the protrusion and recess of those figures has been removed and the cylinder (and cylindrical hole) faceted with longitudinally extending facets that extend the length of the cylinder and cylindrical hole. Facets shall mean flat planar surfaces.

Instead of the circular cylinder and hole arrangement shown in FIGS. 25–26, the cylinder (and the hole that receives) it may be faceted, defining mating surfaces with longitudinally extending interengaging facets that provide the anti-rotation feature of the mating slots and projections (FIG. 30). If faceted, the facets on the cylinder and in the hole in which it is inserted preferably define a regular polygon when viewed along the longitudinal axis of the implant.

The circular cylindrical hole and mating cylinder need not be circular, but can be ovoid, elliptical, or have any other smooth curvilinear irregular surface that assists in preventing rotation of the abutment with respect to the fixture.

Figure 31:
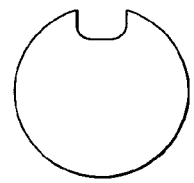
FIG. 31 is an alternative profile of the cylinder and cylindrical hole in the foregoing figures showing the position of the protrusion and the slot reversed: the cylinder extending downward from the upper portion of the implant has a hemispherical slot and the cylindrical hole in the lower portion of the implant has an inwardly extending hemispherical protrusion.

The cylinder, whether extending downward from the abutment, or alternatively extending upward from the fixture, need not have protruding surfaces that engage slots or grooves on the hole. The protrusions or projections 215 may be provided on the inner surface of the hole, extending inwardly, and the slots or groves to which they are mated may be provide on the outer surface of the cylinder. See FIG. 31, for example. In short, the slots 190 and projections 215 may be reversed. Any of the above arrangements and configurations of the mating surfaces of the abutment and the fixture can be combined to provide additional anti-rotation capability.

FIGS. 32–59 illustrate two-piece implants that are preferred as replacement for cuspids. FIGS. 32–45 illustrate a preferred replacement implant for an upper (i.e. maxillary) cuspid 500 and FIGS. 46–59 illustrate a preferred implant for a lower (i.e. mandibular) cuspid implant 502.

The cuspid implants are preferably two piece implants, as illustrated herein, and have coupling structures such as those shown in FIGS. 25–31, described above. While they are illustrated as two-piece implants, they may also be provided in single piece form. In single piece form, they would have the identical structural characteristics, capabilities and features as the two piece upper central incisor implant shown in FIGS. 25–31, but would lack the coupling feature (i.e., the holes, cylinders and screws) of FIGS. 25–31.

Figure 32:
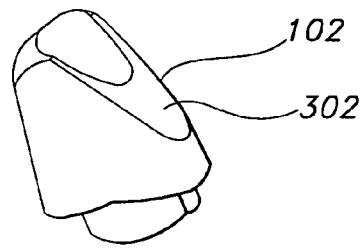
Figure 33:
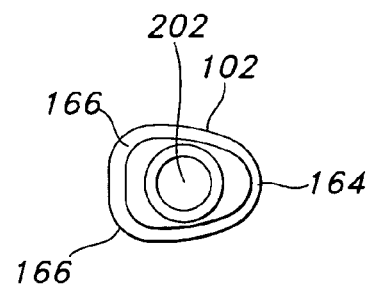
Figure 34:
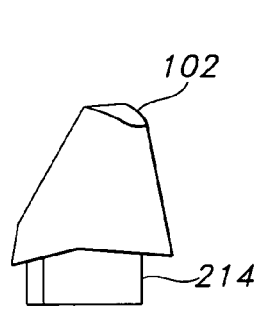
Figures 35, 36:
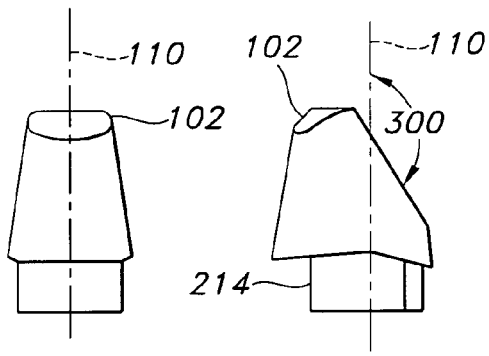
Figure 37:
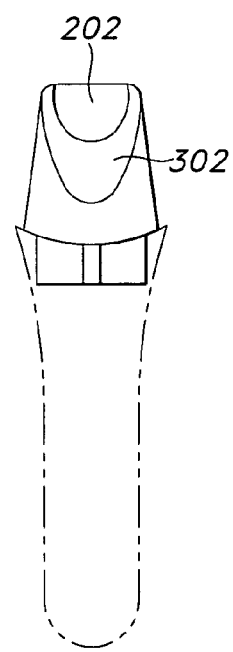
Figure 38:
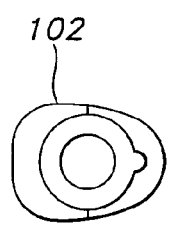
Figure 39:
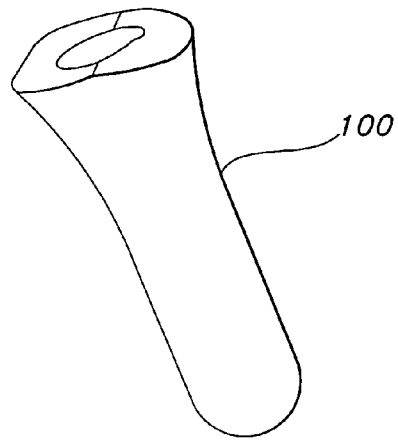
Figure 40:
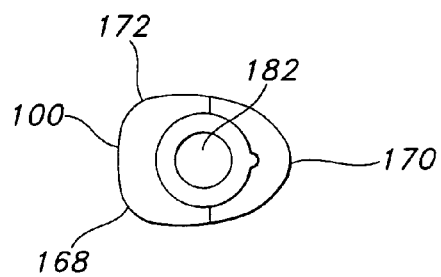
Figure 41:
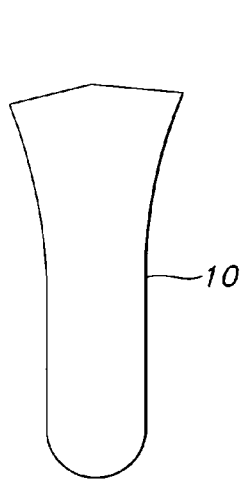
Figures 42, 43:
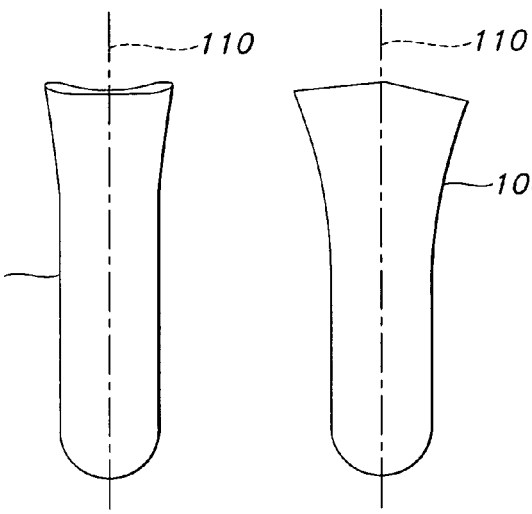
Figure 44:
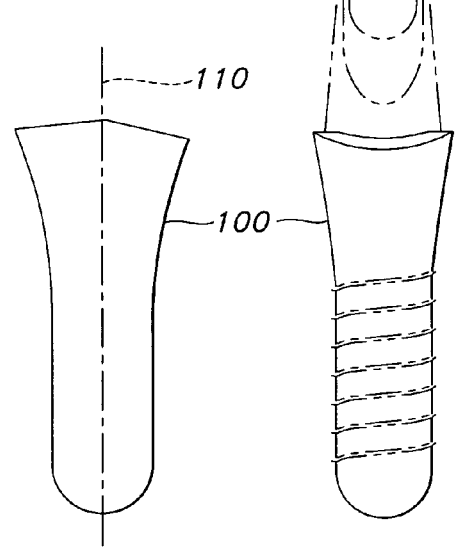
Figure 45:
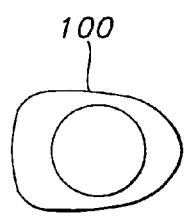
Figure 46:
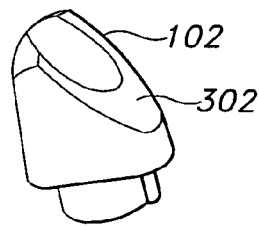
Figure 47:
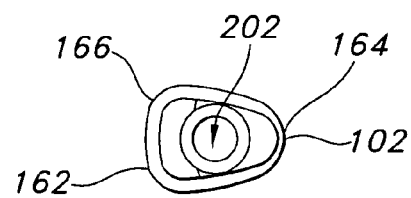
Figure 48:
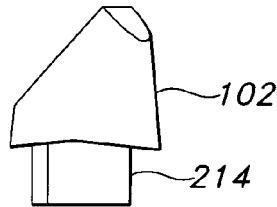
Figure 49:
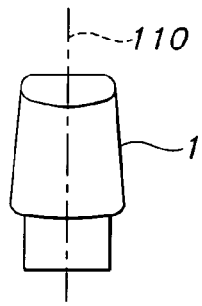
Figure 50:
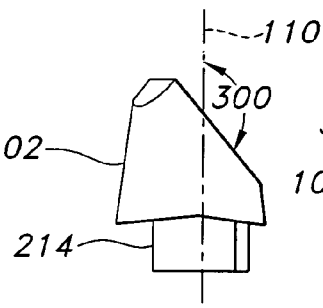
Figure 51:
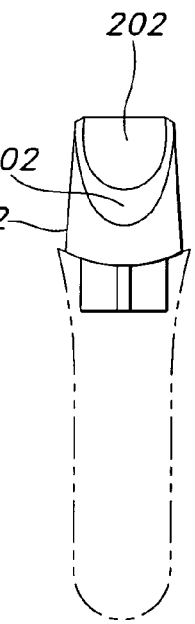
Figure 52:
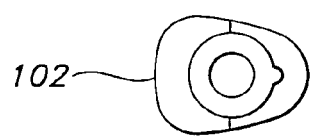
Figure 53:
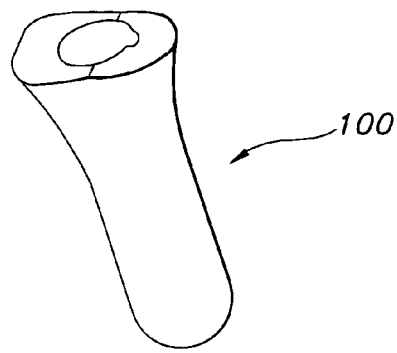
Figure 54:
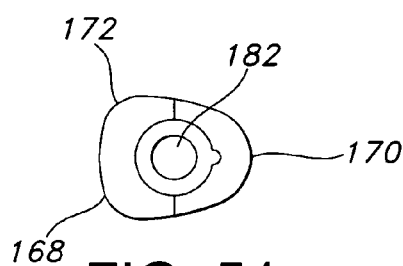
Figure 55:
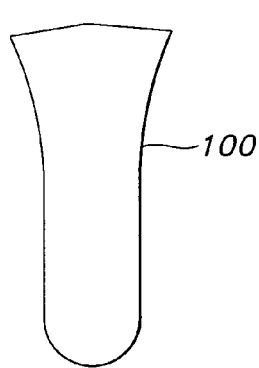
Figure 56:
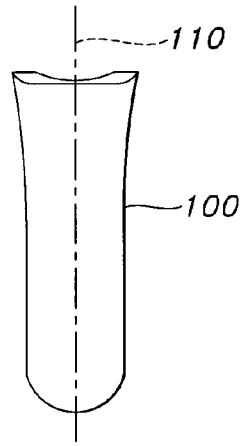
Figure 57:
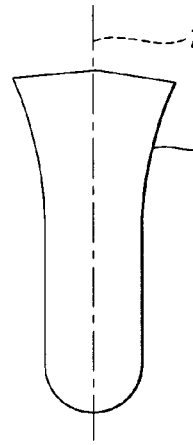
Figure 58:
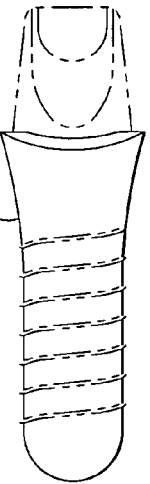
Figure 59:
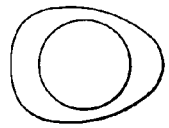
Figure 74:
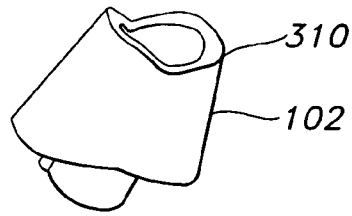
Figure 75:
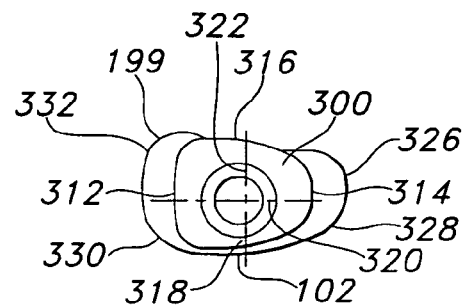
Figure 76:
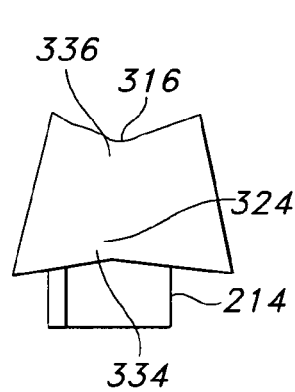
Figures 77, 78:
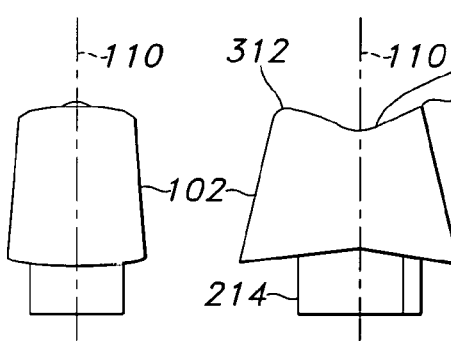
Figure 79:
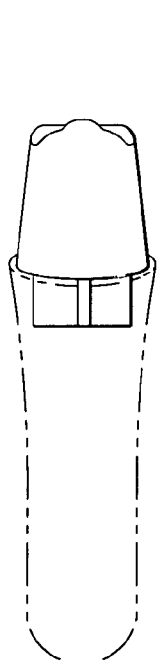
Figure 80:
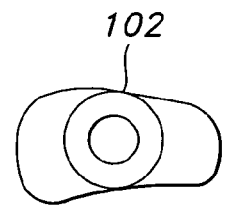
Figure 81:
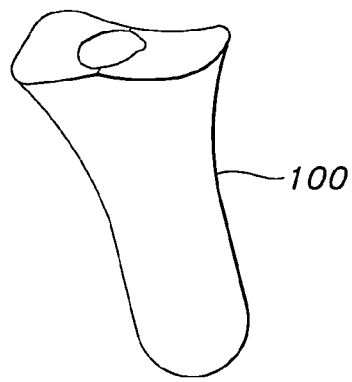

All the two piece implants (FIGS. 25A et seq.), when assembled, have the same configuration, structures, benefits, shapes, sizes, orientations, and uses as the single piece implants of FIGS. 1–24, and differ only in the preferred differential characteristics identified in the discussions accompanying each of the FIGS. 32 et. seq. below. Furthermore, each of the two piece fixtures of FIGS. 32 et seq. preferably have the same illustrated and alternative coupling structures as described above in conjunction with FIGS. 25A–31.

The angle 300 of the planar top 302 of abutment 102 through which hole 202 passes is 135 to 165 degrees with respect to the longitudinal axis 110 of the implant for the upper cuspid and 180 to 150 degrees with respect to the longitudinal axis 510 of the implant for the lower cuspid.

FIGS. 60–73 illustrate a two-piece implant that is preferred as replacement for first lower premolars (FLP). FIGS. 60–66 illustrate the abutment portion 102 and FIGS. 67–73 illustrate the fixture portion 100. Abutment 102 has an upper surface 302 that unlike the prior examples is not a flat plane, but is a compound concave convex surface as shown in the side view of FIG. 64. A lower portion of surface 302 is disposed at an angle 300 with respect to longitudinal axis 110 of 120 degrees. An upper portion of surface 302 is disposed at an angle 300 prime with respect to longitudinal axis 110 of 160 degrees. An upper portion 304 of surface 302 is concave. A lower portion 306 of surface 302 is convex.

FIGS. 74–87 illustrate a two-piece implant that is preferred as a replacement for first upper premolars (FUP). FIGS. 74–80 illustrate the abutment 102 portion of the implant and FIGS. 81–87 illustrate the fixture 100 portion of the implant.

Abutment 102 has an upper surface 310 that defines 2 local maxima 312 and 314 and 2 local minima 316 and 318. These are arranged such that the 2 maxima 312 and 314 are generally aligned with and extend along the fore-and-aft axis 320 and the 2 minima 316 and 318 are disposed along the orthogonal side to side axis 322. In this context, fore-and-aft refers to an axis extending from the lingual side to the labial side of the implant and side to side refers to an axis extending perpendicular to that direction along the mandible or maxilla toward adjacent teeth.

In plan view, upper surface 300 of abutment 102 is convex. The lower portion 159 of abutment 102 as seen in plan view (FIG. 75) is convex-concave. It generally has a kidney shape with one side wall 324 that is concave. The lower portion 159 of abutment 102 has four nodes 326, 328, 330, and 332 generally disposed at the four corners of the abutment with two nodes 330 and 332 facing outward on the labial side and two nodes 326 and 328 facing inwards on the lingual side of the abutment. Side wall 324 changes from concave at a lower portion 334 of the side wall to convex at an upper portion 336 of the side wall.

Figure 82:
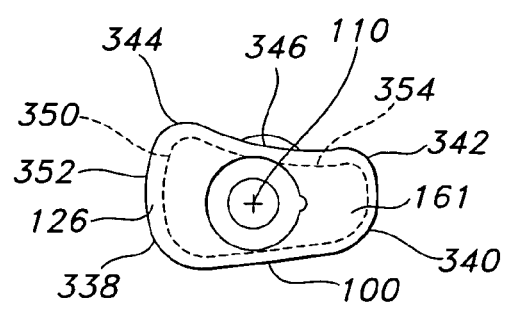
Figures 83, 84, 85, 86:
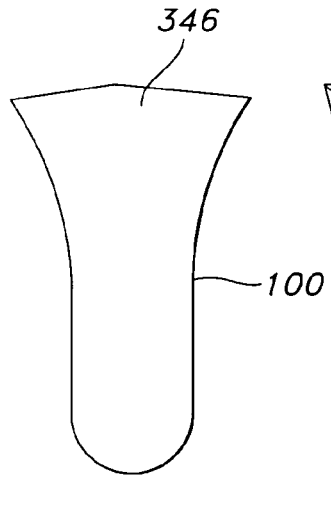
Figure 87:
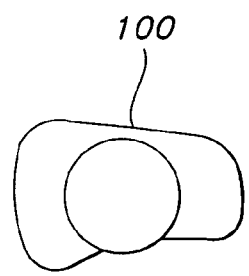
Figure 88:
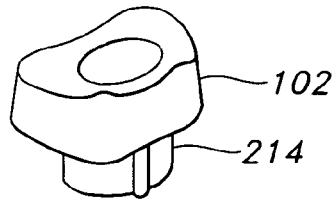
Figure 89:
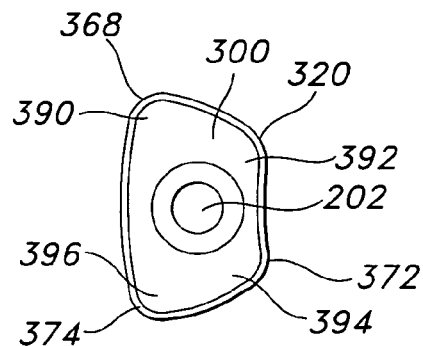
Figure 90:
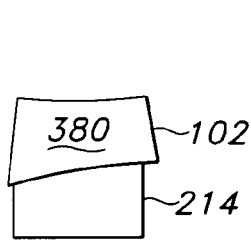
Figures 91, 92:
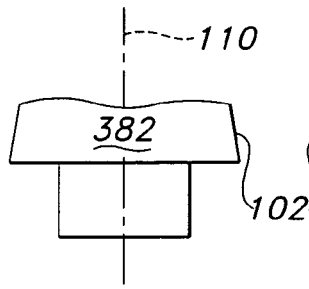
Figure 93:
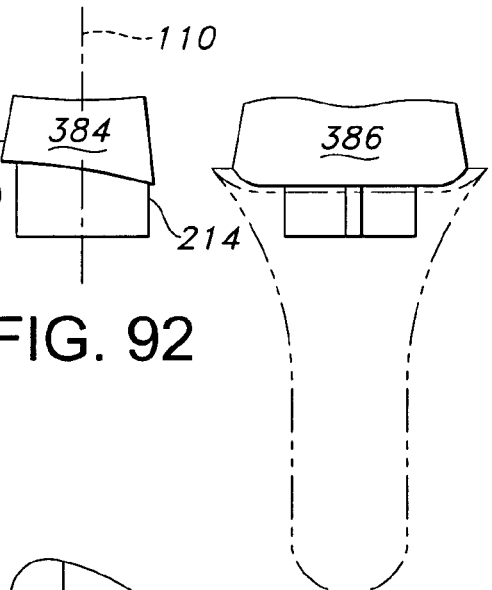
Figure 94:
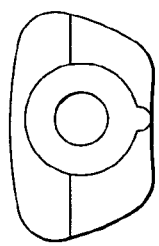
Figure 95:
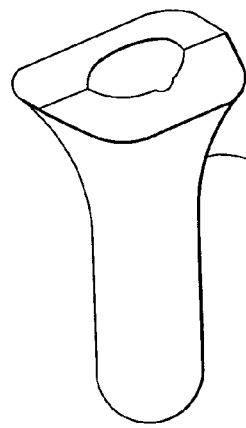
Figure 96:
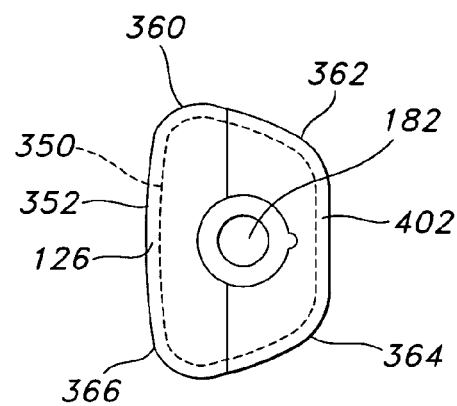
Figure 97:
Figure 98:
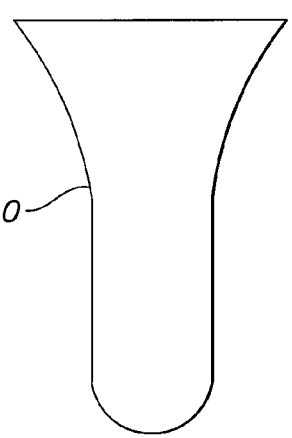
Figure 99:
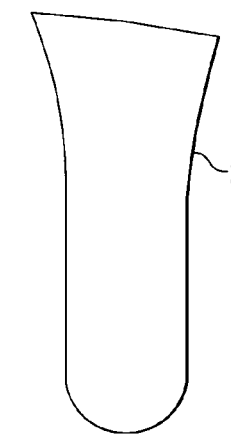
Figure 100:
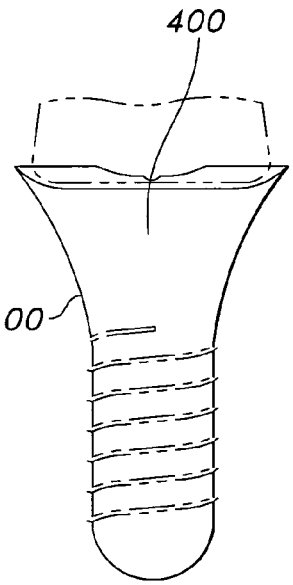
Figure 101:
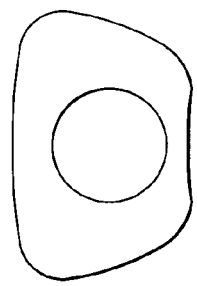

Abutment 100 similarly has an upper surface 161 that is concavo-convex in plan view (FIG. 82). Surface 161 has four nodes 338, 340, 342, and 344 that are disposed about longitudinal axis 110 in the same angular orientation as corresponding nodes 330, 328, 326, and 332, respectively. In a similar fashion, an upward wall portion 346 is concave and is angularly disposed with respect to longitudinal axis 110 in the same location as concave portion 334 of surface 324 of abutment 102 shown in FIG. 74–80. Nodes 338 and 334 face outwardly on a labial wall of the fixture 100 and nodes 340 and 342 face inwardly (lingually) on the opposing side of abutment 100. Top surface 161 of abutment 100 has a kidney shape oriented in the same manner as the kidney shape lower portion 159 of abutment 102.

The fixture concavity and the abutment concavity are preferably disposed one above the other at the same angular location and on the same side of the implant. In the example shown here, the concavity is on the right side of the implant. The right side of the implant is also the side of the implant closes to the front of the mouth. It is the side of the implant that, when inserted, will face and abut either the first upper cuspid or a first upper cuspid implant.

The shape of the concavity is preferably sized to receive a portion of the convex side of the adjacent cuspid. In this manner, the concavity permits the cuspid and the first premolar to be fitted together more closely, with a convex sidewall of the cuspid tooth or implant nested inside the concavity of the first upper premolar.

The concavity of the abutment is similarly reduced as one moves in the opposite direction by rising upward from the concave region toward the top of the abutment. Just as with the fixture, this transition from concavity to convexity is gradual, with the radius of curvature gradually increasing until the wall of the abutment flattens. Above the height that it flattens, the sidewall of the abutment becomes convex. At the same time, the cross-sectional shape becomes rounder, and the four nodes are reduced to three nodes at the top of the abutment, as best shown in the top view of the abutment, FIG. 75.

FIG. 82 includes a dashed line 350 that shows the position of lower portion 159 of abutment 102. The space between line 350, the outer most extent of the lower portion of the abutment and upper edge 352 of fixture 100 defines the narrow band 126 in this example. Note that narrow band 126 when projected in the top view (FIG. 82) is concavo-convex and includes an indented or concaved portion 354 unlike the preceding examples.

FIGS. 88–101 illustrate a two-piece implant that is preferred as a replacement for lower molars (LM). FIGS. 88–93 illustrate the abutment 102 portion, and FIGS. 94–101 illustrate the fixture 100 portion.

The LM implants have four nodes 360, 362, 364, and 366 at the top of the fixture 161, four corresponding nodes 368, 370, 372, and 374 at the bottom 159 of the abutment 102. These nodes on the abutment are angularly aligned with the nodes on the fixture at the bottom of the abutment, and at the top of the abutment. These four nodes are disposed at four angular locations measured in a circumferential direction with respect to the longitudinal axis 110 of the LM implant.

The rounded corners of the abutment 102 that define the nodes typically extend upward and tilt slightly inward, as shown in the FIGURES, to make a four-sided generally pyramidal structure.

The abutment may be a polygonal (preferably quadrilateral and more preferably trapezoidal) pyramidal cylinder with rounded corners, as shown herein. Each face of the pyramidal shape 383, 382, 384, and 386 is a sidewall of the abutment. Each sidewall preferably meets at a corner. These corners where adjacent sidewalls of the abutment meet are rounded. Each corner is one of the four nodes of the abutment.

One sidewall of the abutment, the lingual sidewall 386 faces inward toward the tongue. One sidewall, the facial sidewall 382 faces outward toward the face. The lingual sidewall is preferably shorter than the facial sidewall. The sidewalls 380 and 384 that join the lingual and facial sidewalls therefore spread apart as they extend forward from the lingual sidewall to the facial sidewall.

The top surface 300, while generally planar and parallel to the longitudinal axis of the implant, has four prominences or peaks 390, 392, 394, and 396 that extend upward from the top surface 300 of the abutment 102. These prominences or peaks (local maxima) are disposed one at each rounded corner of the abutment.

The width of the LM implant's narrow band 126 is preferably between 0.5 and 1 mm.

Inner or lingual side wall 386 of abutment 102 is preferably slightly concave, both at the top and at the bottom where it abuts the top of fixture 100. Upper portion 400 of the side wall of fixture 100 is preferably also concave to the same extent as the concavity of abutment 102 thereby defining there between a slightly concave portion 402 of narrow band 126. This concave portion 402 of narrow band 126 is located on the lingual side of the implant fixture 100.

FIGS. 102–115 illustrate a two-piece implant that is preferred as a replacement for upper molars (UM). FIGS. 102–108 illustrate the abutment 102 portion of the UM implant and FIGS. 109–115 illustrate the fixture 100 portion of the UM implant.

The UM implant have three nodes 410, 412, and 414 located at the bottom 159 of abutment 102. There are three corresponding nodes 416, 418, and 420 that are angularly disposed about longitudinal axis 110 in the same location as corresponding nodes 410, 412, and 414. UM abutment 102 has four peaks or prominences (or maxima) that extend upward from top surface 300 of that abutment. Each of these four prominences 430, 432, 434, and 436 are spaced apart from adjacent peaks or prominences by an angle of between 70 and 120 degrees about longitudinal axis 110.

We claim:

1. A dental implant in the form of an elongate body, said implant having a longitudinal axis, the implant comprising:
    a generally cylindrical upper abutment portion having an upper end, a lower end, and an outer wall extending between the upper and lower ends and generally tapering inward toward the longitudinal axis;
    a generally cylindrical and elongate lower fixture portion having a lower end and an upper end, where in said lower end is configured to be inserted into a maxilla or mandible; and
    a flaring upper fixture portion having a lower end and an upper end, said lower end of said fixture portion being formed integral with the upper end of the lower fixture portion, and said upper end of said upper fixture portion being coupled to the lower end of said upper abutment portion;
    wherein the upper end of the upper fixture portion includes a generally axially extending and upwardly-facing planar surface that is revolved about the periphery of the implant, the upper end of the upper abutment portion defining at least two and no more than four first lobes, wherein each of the at least two first lobes are aligned with a corresponding lobe on the upper end of the upper fixture portion.

2. The dental implant of claim 1, wherein the lower fixture portion is circular or polygonal in cross section.

3. The dental implant of claim 1, wherein the planar surface has a substantially constant planar extent as measured in an axial direction.

4. The dental implant of claim 1, wherein the planar surface is symmetric about a symmetry plane perpendicular to a mesial-distal line through said implant.

5. The dental implant of claim 1, wherein the upper abutment portion of the implant has a mesial wall that is concave.

6. The dental implant of claim 1, wherein the upwardly-facing planar surface has a facial portion and a lingual portion, and further wherein the lingual portion descends to a first minimum adjacent the front of the implant.

7. The dental implant of claim 6, wherein the facial portion descends to a second minimum adjacent the rear of the implant.

8. The dental implant of claim 7, wherein the facial portion and the lingual portion are coupled on the distal side at a first local maximum and coupled on the mesial side at a second local maximum.

9. The dental implant of claim 8, wherein the facial portion is in the form of a first plane and the lingual portion is in the form of a second plane, and further wherein the first and second planes intersect on the mesial side of the implant on the distal side of the implant.

10. The dental implant of claim 9, wherein the facial and lingual portions intersect at a first point on the distal side of the implant and a second point on the mesial side of the implant, and further wherein the first and second points of intersection are disposed axially above the first and second minimum.

11. A dental implant in the form of an elongate body, said implant having a longitudinal axis, the implant comprising:
    a generally cylindrical upper abutment portion having an upper end, a lower end, and an outer wall extending between the upper and lower ends and generally tapering inward toward the longitudinal axis;
    a generally cylindrical and elongate lower fixture portion having a lower end and an upper end, where in said lower end is configured to be inserted into a maxilla or mandible; and
    a flaring upper fixture portion having a lower end and an upper end, said lower end of said fixture portion being formed integral with the upper end of the lower fixture portion, and said upper end of said upper fixture portion being coupled to the lower end of said upper abutment portion;
    wherein the upper end of the upper fixture portion includes a generally axially extending and upwardly-facing planar surface that is revolved about the periphery of the implant, the upper end of the upper abutment portion defining at least two and no more than four first lobes, and further wherein an axial cross-section of the lower end of the upper abutment portion has at least three and no more than 4 second lobes disposed radially about the upper abutment portion.

12. The dental implant of claim 11, wherein an axial cross-section of the upper end of the upper fixture portion has at least three and no more than four third lobes in an axial cross section, each of said third lobes being disposed radially about the implant in a position corresponding to an associated one of said second lobes.

13. A dental implant in the form of an elongate body, said implant having a longitudinal axis, the implant comprising:
  a generally cylindrical upper abutment portion having an upper end, a lower end, and an outer wall extending between the upper and lower ends and generally tapering inward toward the longitudinal axis;
  a generally cylindrical and elongate lower fixture portion having a lower end and an upper end, where in said lower end is configured to be inserted into a maxilla or mandible; and
  a flaring upper fixture portion having a lower end and an upper end, said lower end of said fixture portion being formed integral with the upper end of the lower fixture portion, and said upper end of said upper fixture portion being coupled to the lower end of said upper abutment portion;
  wherein the upper end of the upper fixture portion includes a generally axially extending and upwardly-facing planar surface that is revolved about the periphery of the implant, the upper end of the upper abutment portion defining at least two and no more than four first lobes, wherein the planar surface has a substantially constant planar extent as measured in an axial direction, and further wherein the planar surface has a plurality of nodes.

14. The dental implant of claim 13, wherein the plurality of nodes includes at least three nodes with at least two of said plurality of nodes disposed on a front side of said implant and at least one of said plurality of nodes disposed on a back side of said implant.

15. A dental implant in the form of an elongate body, said implant having a longitudinal axis, the implant comprising:
  a generally cylindrical upper abutment portion having an upper end, a lower end, and an outer wall extending between the upper and lower ends and generally tapering inward toward the longitudinal axis;
  a generally cylindrical and elongate lower fixture portion having a lower end and an upper end, where in said lower end is configured to be inserted into a maxilla or mandible; and
  a flaring upper fixture portion having a lower end and an upper end, said lower end of said fixture portion being formed integral with the upper end of the lower fixture portion, and said upper end of said upper fixture portion being coupled to the lower end of said upper abutment portion;
  wherein the upper end of the upper fixture portion includes a generally axially extending and upwardly-facing planar surface that is revolved about the periphery of the implant, the upper end of the upper abutment portion defining at least two and no more than four first lobes, wherein the planar surface is symmetric about a symmetry plane perpendicular to a mesial-distal line through said implant, and further wherein the planar surface defines a first plurality of nodes in plan view and at least one of said first plurality of nodes is disposed on a first side of said symmetry plane and at least one of said first plurality of nodes is disposed on a second side of said symmetry plane.

16. The dental implant of claim 15, wherein at least one node of said first plurality of nodes is bisected by said symmetry plane.

17. The dental implant of claim 15, wherein at least two of said first plurality of nodes are disposed on a first side of said symmetry plane and at least two of said first plurality of nodes are disposed on a second side of said symmetry plane.

18. A dental implant in the form of an elongate body, said implant having a longitudinal axis, the implant comprising:
  a generally cylindrical upper abutment portion having an upper end, a lower end, and an outer wall extending between the upper and lower ends and generally tapering inward toward the longitudinal axis;
  a generally cylindrical and elongate lower fixture portion having a lower end and an upper end, where in said lower end is configured to be inserted into a maxilla or mandible; and
  a flaring upper fixture portion having a lower end and an upper end, said lower end of said fixture portion being formed integral with the upper end of the lower fixture portion, and said upper end of said upper fixture portion being coupled to the lower end of said upper abutment portion;
  wherein the upper end of the upper fixture portion includes a generally axially extending and upwardly-facing planar surface that is revolved about the periphery of the implant, the upper end of the upper abutment portion defining at least two and no more than four first lobes, wherein the upper abutment portion of the implant has a mesial wall that is concave, and further wherein a lower portion of the mesial wall is concave and an upper portion of the mesial wall is convex.

19. The dental implant of claim 18, wherein the upper abutment portion of the implant has a distal wall that is concave.

20. The dental implant of claim 19, wherein a lower portion of the distal wall that is coaxial with the upper portion of the mesial wall, is convex.

21. The dental implant of claim 20, wherein a lower portion of the distal wall that is coaxial with the lower portion of the mesial wall, is convex.

22. The dental implant of claim 18, wherein the fixture portion of the implant has a mesial wall that is concave.

23. The dental implant of claim 22, wherein an upper portion of said mesial wall of said fixture portion is concave and a lower portion of said mesial wall of said fixture portion is convex.

24. The dental implant of claim 23, wherein an axial cross-section of said fixture portion coaxial with said lower portion of said mesial wall is circular.

25. A dental implant in the form of an elongate body, said implant having a longitudinal axis, the implant comprising:
  a generally cylindrical upper abutment portion having an upper end, a lower end, and an outer wall extending between the upper and lower ends and generally tapering inward toward the longitudinal axis;
  a generally cylindrical and elongate lower fixture portion having a lower end and an upper end, where in said lower end is configured to be inserted into a maxilla or mandible; and
  a flaring upper fixture portion having a lower end and an upper end, said lower end of said fixture portion being formed integral with the upper end of the lower fixture portion, and said upper end of said upper fixture portion being coupled to the lower end of said upper abutment portion;

wherein the upper end of the upper fixture portion includes a generally axially extending and upwardly-facing planar surface that is revolved about the periphery of the implant, the upper end of the upper abutment portion defining at least two and no more than four first lobes, and further wherein a first axial cross-section of said abutment portion of said implant is kidney-shaped.

26. A dental implant in the form of an elongate monolithic body, said implant having a longitudinal axis, the implant comprising:
- a generally cylindrical upper abutment portion having an upper end, a lower end, and an outer wall extending between the upper and lower ends and generally tapering inward toward the longitudinal axis;
- an elongate lower fixture portion having a lower end and an upper end, wherein said lower end is configured to be inserted into a maxilla or mandible; and
- a flaring upper fixture portion having a lower end and an upper end, said lower end of said fixture portion being formed integral with the upper end of the lower fixture portion, and said upper end of said upper fixture portion being coupled to the lower end of said upper abutment portion;
- wherein the upper end of the upper fixture portion includes a generally axially extending and upwardly-facing planar surface that is revolved about the periphery of the implant,
- wherein the upper end of the upper fixture portion has a first plurality of lobes numbering at least two and no more than four;
- wherein the lower end of the upper abutment portion has a second plurality of lobes numbering at least two and no more than four, and further wherein the each of the first plurality of lobes is aligned with a corresponding one of the second plurality of lobes.

* * * * *